United States Patent
Furuya et al.

(10) Patent No.: US 7,910,735 B2
(45) Date of Patent: Mar. 22, 2011

(54) SUBSTITUTED PYRAZINECARBOXYLIC ACID ANILIDE DERIVATIVES OR SALTS THEREOF, INTERMEDIATES OF THE SAME, PESTICIDES FOR AGRICULTURAL AND HORTICULTURAL USE, AND USAGE THEREOF

(75) Inventors: Takashi Furuya, Kawachinagano (JP);
Kozo Machiya, Kawachinagano (JP);
Akiyuki Suwa, Kawachinagano (JP);
Shinsuke Fujioka, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 1156 days.

(21) Appl. No.: 11/597,185

(22) PCT Filed: May 26, 2005

(86) PCT No.: PCT/JP2005/009667
§ 371 (c)(1),
(2), (4) Date: Nov. 21, 2006

(87) PCT Pub. No.: WO2005/115994
PCT Pub. Date: Dec. 8, 2005

(65) Prior Publication Data
US 2008/0064708 A1    Mar. 13, 2008

(30) Foreign Application Priority Data
May 27, 2004 (JP) .................. 2004-157634

(51) Int. Cl.
*C07D 241/02* (2006.01)
(52) U.S. Cl. ....................................... 544/406
(58) Field of Classification Search ............. 544/406
See application file for complete search history.

(56) References Cited

U.S. PATENT DOCUMENTS

| 2004/0058964 A1 | 3/2004 | Devadas et al. |
| 2005/0113400 A1 | 5/2005 | Chaki et al. |

FOREIGN PATENT DOCUMENTS

| EP | 0936212 A1 | 8/1999 |
| EP | 1188745 A1 | 3/2002 |
| EP | 1400516 A1 | 3/2004 |
| WO | WO 99/12933 A2 | 3/1999 |

*Primary Examiner* — Sharmila Gollamudi Landau
*Assistant Examiner* — Kortney L Klinkel
(74) *Attorney, Agent, or Firm* — Paul E. White, Jr.; Manelli Denison & Selter PLLC

(57) ABSTRACT

Substituted pyrazinecarboxylic acid anilide derivatives represented by the general formula (I) or salts thereof; intermediates of them; pesticides (such as insecticides and acaricides) for agricultural and horticultural use, containing the compounds as the active ingredient; and usage thereof:

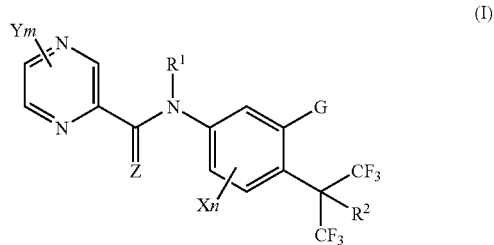

wherein $R^1$ is H, $C_{1-6}$ alkyl, halo $C_{1-6}$ alkyl, or the like; $R^2$ is halogeno, $C_{1-6}$ alkyl, or the like; G is $C_{2-10}$ alkyl or the like; Z is oxygen or sulfur; X's are each independently H, halogeno, or the like; Y's are each independently H, halogeno, cyano, or the like; and m and n are each an integer of 1 to 3.

1 Claim, No Drawings

SUBSTITUTED PYRAZINECARBOXYLIC ACID ANILIDE DERIVATIVES OR SALTS THEREOF, INTERMEDIATES OF THE SAME, PESTICIDES FOR AGRICULTURAL AND HORTICULTURAL USE, AND USAGE THEREOF

This application is the national phase of international application PCT/JP2005/009667 filed 26 May 2005 which designated the U.S.

TECHNICAL FIELD

The present invention relates to substituted pyrazinecarboxanilide derivatives or salts thereof, intermediates thereof, and agrohorticultural agents containing the substituted pyrazinecarboxanilide derivatives or salts thereof as an active ingredient, and more particularly, insecticides or acaricides, and method for use thereof.

BACKGROUND ART

Heretofore, substituted anilide derivatives similar to those of the present invention have been known to be useful as the agrohorticultural insecticides, fungicides or acaricides (e.g. refer to JP-A-2003-48878). However, number of examples is limited and compounds of the present invention are not disclosed specifically. In the heterocyclic carboxylic acid moiety of the compounds, neither examples of compounds, to which a pyrazine ring disclosed in the present invention is introduced, nor descriptions of the compounds in a compound list are found. Further, with regard to a substituent at aniline moiety, only a methyl group at 3-position is described as a substituent in an example, and neither examples of the compound, to which an alkyl group having two or more carbon atoms are introduced into the 3-position as described in the present invention, nor descriptions of such compounds in a compound list are found. Furthermore, a specifically disclosed one having a methyl substituent at 3-position exhibits no acaricidal activity.

DISCLOSURE OF INVENTION

Problem to be Solved by the Invention

In crop manufacturing in agricultural and horticultural fields, damages caused by insect pests are still serious, and development of novel agrohorticultural agents, particularly development of insecticides and acaricides is desired due to generation of insect pests resistant to known agents. Since various labor saving farm works are required due to increasing numbers of the aged farm working population, creation of agrohorticultural agents with properties suitable for such labor saving farm work, particularly insecticides and acaricides, is also demanded.

Means for Solving the Problem

The inventors of the present invention have continued extensive studies on development of novel agrohorticultural agents, particularly insecticides and acaricides and have found, as the result, that among broad range of compounds described in the aforementioned prior document, a substituted pyrazinecarboxanilide derivative represented by the general formula (I), in which a pyrazine ring is selected as the heterocyclic carboxylic acid moiety and a specific substituent is introduced into the aniline moiety at 3-position, showed excellent control effect as acaricides, not predicted at all from the content described in the prior art references. Further, the inventors have found that an intermediate of said compound, i.e. a substituted aniline derivative represented by the general formula (II), and a substituted pyrazinecarboxylic acid derivative represented by the general formula (III') were novel compounds unknown in prior references, and were useful as intermediates for manufacturing various derivatives having physiological activities of pharmaceuticals and pesticides, and thus completed the present invention.

That is the present invention relates to a substituted pyrazinecarboxanilide derivative or salt thereof represented by the general formula (I):

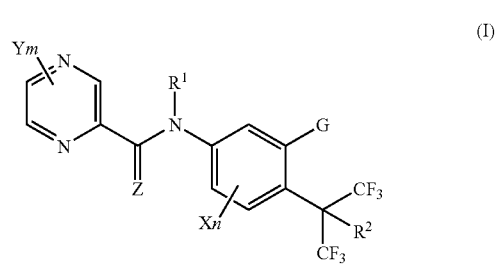

(I)

(wherein $R^1$ represents a hydrogen atom; a $C_1$-$C_6$ alkyl group; a halo $C_1$-$C_6$ alkyl group; a $C_1$-$C_6$ alkylcarbonyl group; a halo $C_1$-$C_6$ alkylcarbonyl group; a $C_1$-$C_6$ alkylcarbonyl $C_1$-$C_6$ alkyl group; a $C_3$-$C_6$ cycloalkyl group; a $C_3$-$C_6$ halocycloalkyl group; a $C_3$-$C_6$ cycloalkyl $C_1$-$C_6$ alkyl group; a $C_3$-$C_6$ halocycloalkyl $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a $C_1$-$C_6$ alkoxy $C_1$-$C_6$ alkyl group; a halo $C_1$-$C_6$ alkoxy $C_1$-$C_6$ alkyl group; a $C_1$-$C_6$ alkoxy $C_1$-$C_6$ alkoxyl $C_1$-$C_6$ alkyl group; a $C_1$-$C_6$ alkylthio $C_1$-$C_6$ alkyl group; a halo $C_1$-$C_6$ alkylthio $C_1$-$C_6$ alkyl group; a $C_1$-$C_6$ alkylsulfinyl $C_1$-$C_6$ alkyl group; a halo $C_1$-$C_6$ alkylsulfinyl $C_1$-$C_6$ alkyl group; a $C_1$-$C_6$ alkylsulfonyl $C_1$-$C_6$ alkyl group; a halo $C_1$-$C_6$ alkylsulfonyl $C_1$-$C_6$ alkyl group; a mono $C_1$-$C_6$ alkylamino $C_1$-$C_6$ alkyl group; a di $C_1$-$C_6$ alkylamino $C_1$-$C_6$ alkyl group in which the alkyl groups are same or different; a phenyl $C_1$-$C_6$ alkoxy $C_1$-$C_6$ alkyl group; a $C_1$-$C_6$ alkoxycarbonyl group; a $C_1$-$C_6$ alkoxy $C_1$-$C_6$ alkoxycarbonyl group; a halo $C_1$-$C_6$ alkoxycarbonyl group; a $C_1$-$C_6$ alkylthiocarbonyl group; a mono $C_1$-$C_6$ alkylaminocarbonyl group; a di $C_1$-$C_6$ alkylaminocarbonyl group in which the alkyl groups are same or different; a $C_1$-$C_6$ alkoxycarbonyl $C_1$-$C_6$ alkyl group; a $C_1$-$C_6$ alkylsulfonyl group; a halo $C_1$-$C_6$ alkylsulfonyl group; a cyano $C_1$-$C_6$ alkyl group; a phenyl $C_1$-$C_6$ alkyl group; a substituted phenyl $C_1$-$C_6$ alkyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenoxycarbonyl group; a substituted phenoxycarbonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfonyl group; a substituted phenylsulfonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a di $C_1$-$C_6$ alkylphosphono group in which the alkyl groups are same or different; a di $C_1$-$C_6$ alkylphosphonothio group in which the alkyl groups are same or different; N—$C_1$-$C_6$ alkyl-N—$C_1$-$C_6$ alkoxycarbonylaminothio group; N—$C_1$-$C_6$ alkyl-N—$C_1$-$C_6$ alkoxycarbonyl $C_1$-$C_6$ alkylaminothio group; a di $C_1$-$C_6$ alkylaminothio group in which the alkyl groups are same or different; or a $C_3$-$C_6$ cycloalkylcarbonyl group;

$R^2$ represents a hydrogen atom; a halogen atom; a $C_1$-$C_6$ alkyl group; a halo $C_1$-$C_6$ alkyl group; a cyano group; a hydroxyl group; a $C_1$-$C_6$ alkoxyl group; a halo $C_1$-$C_6$ alkoxyl group; a $C_1$-$C_6$ alkoxy $C_1$-$C_3$ alkoxyl group; a halo $C_1$-$C_6$ alkoxy $C_1$-$C_3$ alkoxyl group; a $C_1$-$C_6$ alkylthio $C_1$-$C_3$ alkoxyl group; a halo $C_1$-$C_6$ alkylthio $C_1$-$C_3$ alkoxyl group; a $C_1$-$C_6$ alkylsulfinyl $C_1$-$C_3$ alkoxyl group; a halo $C_1$-$C_6$ alkylsulfinyl $C_1$-$C_3$ alkoxyl group; a $C_1$-$C_6$ alkylsulfonyl $C_1$-$C_3$ alkoxyl group; a halo $C_1$-$C_6$ alkylsulfonyl $C_1$-$C_3$ alkoxyl group; a mono $C_1$-$C_6$ alkylamino $C_1$-$C_3$ alkoxyl group; a di $C_1$-$C_6$ alkylamino $C_1$-$C_3$ alkoxyl group in which the alkyl groups are same or different; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; an amino group; a mono $C_1$-$C_6$ alkylamino group; a di $C_1$-$C_6$ alkylamino group in which the alkyl groups are same or different; a phenoxy group; a substituted phenoxy group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylthio group; a substituted phenylthio group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfinyl group; a substituted phenylsulfinyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfonyl group; a substituted phenylsulfonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenyl $C_1$-$C_6$ alkoxyl group; or a substituted phenyl $C_1$-$C_6$ alkoxyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group;

G represents a $C_2$-$C_{10}$ alkyl group; a halo $C_2$-$C_{10}$ alkyl group; a $C_3$-$C_{10}$ alkenyl group; a halo $C_3$-$C_{10}$ alkenyl group; a $C_3$-$C_{10}$ alkynyl group; a halo $C_3$-$C_{10}$ alkynyl group; a $C_3$-$C_{10}$ cycloalkyl group; a substituted $C_3$-$C_{10}$ cycloalkyl group having the same or different one or more substituents selected from a halogen atom, a $C_1$-$C_6$ alkyl group and a halo $C_1$-$C_6$ alkyl group; a $C_3$-$C_{10}$ cycloalkenyl group; a substituted $C_3$-$C_{10}$ cycloalkenyl group having the same or different one or more substituents selected from a halogen atom, a $C_1$-$C_6$ alkyl group and a halo $C_1$-$C_6$ alkyl group; a $C_3$-$C_8$ cycloalkyl $C_1$-$C_6$ alkyl group; or a halo $C_3$-$C_8$ cycloalkyl $C_1$-$C_6$ alkyl group;

Z represents an oxygen atom or a sulfur atom;

X may be the same or different and represents a hydrogen atom, a halogen atom, a cyano group, a nitro group, a $C_1$-$C_6$ alkyl group or a halo $C_1$-$C_6$ alkyl group;

Y may be the same or different and represents a hydrogen atom; a halogen atom; a cyano group; a nitro group; a hydroxyl group; a mercapto group; an amino group; a carboxyl group; a $C_1$-$C_6$ alkyl group; a halo $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a tri $C_1$-$C_6$ alkylsilyl $C_2$-$C_6$ alkynyl group in which the alkyl groups are same or different; a phenyl $C_2$-$C_6$ alkynyl group; a $C_1$-$C_6$ alkoxy $C_1$-$C_6$ alkoxy $C_1$-$C_6$ alkyl group; a hydroxy $C_1$-$C_6$ alkyl group; a $C_1$-$C_6$ alkylcarbonyloxy $C_1$-$C_6$ alkyl group; a $C_3$-$C_6$ cycloalkyl group; a $C_3$-$C_6$ halocycloalkyl group; a $C_3$-$C_6$ cycloalkyl $C_1$-$C_6$ alkyl group; a $C_3$-$C_6$ halocycloalkyl $C_1$-$C_6$ alkyl group; a $C_1$-$C_6$ alkoxyl group; a halo $C_1$-$C_6$ alkoxyl group; a $C_1$-$C_6$ alkoxy $C_1$-$C_6$ alkoxyl group; a halo $C_1$-$C_6$ alkoxy $C_1$-$C_6$ alkoxyl group; a phenyl $C_1$-$C_6$ alkoxyl group; a $C_1$-$C_6$ alkoxy $C_1$-$C_6$ alkyl group; a halo $C_1$-$C_6$ alkoxy $C_1$-$C_6$ alkyl group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a $C_1$-$C_6$ alkylthio $C_1$-$C_6$ alkyl group; a halo $C_1$-$C_6$ alkylthio $C_1$-$C_6$ alkyl group; a $C_1$-$C_6$ alkylsulfinyl $C_1$-$C_6$ alkyl group; a halo $C_1$-$C_6$ alkylsulfinyl $C_1$-$C_6$ alkyl group; a $C_1$-$C_6$ alkylsulfonyl $C_1$-$C_6$ alkyl group; a halo $C_1$-$C_6$ alkylsulfonyl $C_1$-$C_6$ alkyl group; a mono $C_1$-$C_6$ alkylamino group; a di $C_1$-$C_6$ alkylamino group in which the alkyl groups are same or different; a phenylamino group; a mono $C_1$-$C_6$ alkylamino $C_1$-$C_6$ alkyl group; a di $C_1$-$C_6$ alkylamino $C_1$-$C_6$ alkyl group in which the alkyl groups are same or different; a phenyl group; a substituted phenyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenoxy group; a substituted phenoxy group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a heterocyclic group; or a substituted heterocyclic group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; and the two adjacent Ys on a pyrazine ring may form a condensed ring each other and said condensed ring may have the same or different one or more substituents selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; and m and n represent integers of 1 to 3), an agrohorticultural agent containing said compounds as an active ingredient and a method of using thereof.

The present invention also relates to an intermediate thereof, that is a substituted aniline derivative or salt thereof represented by the general formula (II):

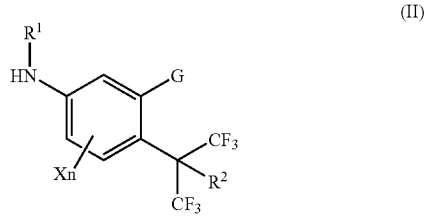

(II)

(wherein $R^1$ represents a hydrogen atom; a $C_1$-$C_6$ alkyl group; a halo $C_1$-$C_6$ alkyl group; a $C_1$-$C_6$ alkylcarbonyl group; a halo $C_1$-$C_6$ alkylcarbonyl group; a $C_1$-$C_6$ alkylcarbonyl $C_1$-$C_6$ alkyl group; a $C_3$-$C_6$ cycloalkyl group; a $C_3$-$C_6$ halocycloalkyl group; a $C_3$-$C_6$ cycloalkyl $C_1$-$C_6$ alkyl group; a $C_3$-$C_6$ halocycloalkyl $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a $C_1$-$C_6$ alkoxy $C_1$-$C_6$ alkyl group; a halo $C_1$-$C_6$ alkoxy $C_1$-$C_6$ alkyl group; a $C_1$-$C_6$ alkoxy $C_1$-$C_6$ alkoxyl $C_1$-$C_6$ alkyl group; a $C_1$-$C_6$ alkylthio $C_1$-$C_6$ alkyl group; a halo $C_1$-$C_6$ alkylthio $C_1$-$C_6$ alkyl group; a $C_1$-$C_6$ alkylsulfinyl $C_1$-$C_6$ alkyl group; a halo $C_1$-$C_6$ alkylsulfinyl $C_1$-$C_6$ alkyl group; a $C_1$-$C_6$ alkylsulfonyl $C_1$-$C_6$ alkyl group; a halo $C_1$-$C_6$ alkylsulfonyl $C_1$-$C_6$ alkyl group; a mono $C_1$-$C_6$ alkylamino $C_1$-$C_6$ alkyl group; a di $C_1$-$C_6$ alkylamino $C_1$-$C_6$ alkyl group in which the alkyl groups are same or different; a phenyl $C_1$-$C_6$ alkoxy $C_1$-$C_6$ alkyl group; a $C_1$-$C_6$ alkoxycarbonyl group; a $C_1$-$C_6$ alkoxy $C_1$-$C_6$ alkoxycarbonyl group; a halo $C_1$-$C_6$ alkoxycarbonyl group; a $C_1$-$C_6$ alkylthiocarbonyl group; a mono $C_1$-$C_6$ alkylaminocarbonyl group; a di $C_1$-$C_6$ alkylaminocarbonyl group in which the alkyl groups are same or different; a $C_1$-$C_6$ alkoxycarbonyl $C_1$-$C_6$ alkyl group; a $C_1$-$C_6$ alkylsulfonyl group; a halo $C_1$-$C_6$ alkylsulfonyl group; a cyano $C_1$-$C_6$ alkyl group; a phenyl $C_1$-$C_6$ alkyl group; a substituted phenyl $C_1$-$C_6$ alkyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenoxycarbonyl group; a substituted phenoxycarbonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfonyl group; a substituted phenylsulfonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a di $C_1$-$C_6$ alkylphosphono group in which the alkyl groups are same or different; a di $C_1$-$C_6$ alkylphosphonothio group in which the alkyl groups are same or different; N—$C_1$-$C_6$ alkyl-N—$C_1$-$C_6$ alkoxycarbonylaminothio group; N—$C_1$-$C_6$ alkyl-N—$C_1$-$C_6$ alkoxycarbonyl $C_1$-$C_6$ alkylaminothio group; a di $C_1$-$C_6$ alkylaminothio group in which the alkyl groups are same or different; or a $C_3$-$C_6$ cycloalkylcarbonyl group;

$R^2$ represents a hydrogen atom; a halogen atom; a $C_1$-$C_6$ alkyl group; a halo $C_1$-$C_6$ alkyl group; a cyano group; a hydroxyl group; a $C_1$-$C_6$ alkoxyl group; a halo $C_1$-$C_6$ alkoxyl group; a $C_1$-$C_6$ alkoxy $C_1$-$C_3$ alkoxyl group; a halo $C_1$-$C_6$ alkoxy $C_1$-$C_3$ alkoxyl group; a $C_1$-$C_6$ alkylthio $C_1$-$C_3$ alkoxyl group; a halo $C_1$-$C_6$ alkylthio $C_1$-$C_3$ alkoxyl group; a $C_1$-$C_6$ alkylsulfinyl $C_1$-$C_3$ alkoxyl group; a halo $C_1$-$C_6$ alkylsulfinyl $C_1$-$C_3$ alkoxyl group; a $C_1$-$C_6$ alkylsulfonyl $C_1$-$C_3$ alkoxyl group; a halo $C_1$-$C_6$ alkylsulfonyl $C_1$-$C_3$ alkoxyl group; a mono $C_1$-$C_6$ alkylamino $C_1$-$C_3$ alkoxyl group; a di $C_1$-$C_6$ alkylamino $C_1$-$C_3$ alkoxyl group in which the alkyl groups are same or different; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; an amino group; a mono $C_1$-$C_6$ alkylamino group; a di $C_1$-$C_6$ alkylamino group in which the alkyl groups are same or different; a phenoxy group; a substituted phenoxy group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylthio group; a substituted phenylthio group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfinyl group; a substituted phenylsulfinyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenylsulfonyl group; a substituted phenylsulfonyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group; a phenyl $C_1$-$C_6$ alkoxyl group; or a substituted phenyl $C_1$-$C_6$ alkoxyl group having the same or different one or more substituents on the ring, selected from a halogen atom, a cyano group, a nitro group, a $C_1$-$C_6$ alkyl group, a halo $C_1$-$C_6$ alkyl group, a $C_1$-$C_6$ alkoxyl group, a halo $C_1$-$C_6$ alkoxyl group, a $C_1$-$C_6$ alkylthio group, a halo $C_1$-$C_6$ alkylthio group, a $C_1$-$C_6$ alkylsulfinyl group, a halo $C_1$-$C_6$ alkylsulfinyl group, a $C_1$-$C_6$ alkylsulfonyl group, a halo $C_1$-$C_6$ alkylsulfonyl group, a mono $C_1$-$C_6$ alkylamino group, a di $C_1$-$C_6$ alkylamino group in which the alkyl groups are same or different and a $C_1$-$C_6$ alkoxycarbonyl group;

G represents a $C_2$-$C_{10}$ alkyl group; a halo $C_2$-$C_{10}$ alkyl group; a $C_3$-$C_{10}$ alkenyl group; a halo $C_3$-$C_{10}$ alkenyl group; a $C_3$-$C_{10}$ alkynyl group; a halo $C_3$-$C_{10}$ alkynyl group; a $C_3$-$C_{10}$ cycloalkyl group; a substituted $C_3$-$C_{10}$ cycloalkyl group having the same or different one or more substituents selected from a halogen atom, a $C_1$-$C_6$ alkyl group and a halo $C_1$-$C_6$ alkyl group; a $C_3$-$C_{10}$ cycloalkenyl group; a substituted $C_3$-$C_{10}$ cycloalkenyl group having the same or different one or more substituents selected from a halogen atom, a $C_1$-$C_6$ alkyl group and a halo $C_1$-$C_6$ alkyl group; a $C_3$-$C_8$ cycloalkyl $C_1$-$C_6$ alkyl group; or a halo $C_3$-$C_8$ cycloalkyl $C_1$-$C_6$ alkyl group;

X may be the same or different and represents a hydrogen atom, a halogen atom, a cyano group, a nitro group, a $C_1$-$C_6$ alkyl group or a halo $C_1$-$C_6$ alkyl group; and n represents an integer of 1 to 3, and also relates to a substituted pyrazinecarboxylic acid derivative or salt thereof represented by the general formula (III'):

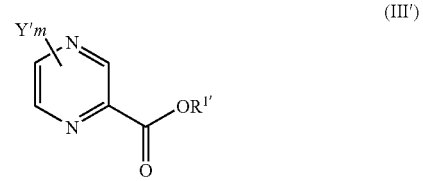

(III')

(wherein Y' may be the same or different and represents a halo $C_1$-$C_6$ alkyl group; $R^{1'}$ represents a hydrogen atom or a $C_1$-$C_6$ alkyl group; and m represents an integer of 1 to 3).

ADVANTAGES OF THE INVENTION

In accordance with the present invention, an agrohorticultural agent, in particular, insecticides or acaricides having superior performance compared with conventional technology can be provided.

BEST MODE FOR CARRYING OUT THE INVENTION

In the definitions of a substituted pyrazinecarboxanilide derivative of the general formula (I), a substituted aniline derivative of the general formula (II) and a substituted pyrazinecarboxylic acid derivative of the general formula (III') of the present invention, "halo", "$C_1$-$C_6$ alkyl", "$C_1$-$C_6$ alkoxyl", "$C_2$-$C_6$ alkenyl", "$C_2$-$C_6$ alkynyl" or "a heterocyclic group", and the like in each of substituents has the following meaning.

"Halo" or "a halogen atom" represents a chlorine atom, a bromine atom, an iodine atom or a fluorine atom. "$C_1$-$C_6$ alkyl" represents a straight chain or branched chain alkyl group with 1 to 6 carbon atoms including, for example, a methyl group, an ethyl group, a n-propyl group, an isopropyl group, a n-butyl group, an isobutyl group, a sec-butyl group, a tert-butyl group, a n-pentyl group and a n-hexyl group. "$C_3$-$C_{10}$ cycloalkyl" represents a cyclic alkyl group with 3 to 10 carbon atoms including, for example, a cyclopropyl group, a cyclobutyl group, a cyclopentyl group, a cyclohexyl group, a cyclooctyl group and a cyclodecyl group. "$C_1$-$C_6$ alkoxyl" represents an alkoxyl group, whose alkyl moiety is the above "$C_1$-$C_6$ alkyl" including, for example, a methoxy group, an ethoxy group, a propoxy group, a butoxy group, an isobutoxy group, a tert-butoxy group, a pentyloxy group and a hexyloxy group. "$C_2$-$C_6$ alkenyl" represents a straight chain or branched chain alkenyl group with 2 to 6 carbon atoms and having at least one double bond including, for example, a vinyl group, a 1-propenyl group, an allyl group, a 1-butenyl group, a 2-butenyl group, a 3-butenyl group, a 2-pentenyl group, a 2,4-pentadienyl group and a 3-hexenyl group. "$C_2$-$C_6$ alkynyl" represents a straight chain or branched chain alkynyl group with 2 to 6 carbon atoms and having at least one triple bond including, for example, an ethynyl group, a 2-propynyl group, a 1-butynyl group, a 2-butynyl group, a 3-butynyl group, a 2-pentynyl group and 3-hexynyl group. Numerical values such as "$C_2$-$C_6$", "$C_3$-$C_{10}$", and the like represents the range of carbon atoms such as carbon atoms of 2 to 6 or 3 to 10. Further, as for a group bonded with the above substituent, the above definitions can be applied, for example, "halo $C_1$-$C_6$ alkyl" represents a straight chain or branched chain alkyl group with 1 to 6 carbon atoms substituted with the same or different one or more halogen atoms including, for example, a difluoromethyl group, a trifluoromethyl group, a 2,2,2-trifluoroethyl group and a perfluorohexyl group.

"A heterocyclic group" represents a 5- or 6-membered heterocyclic group having one or more hetero atoms selected from an oxygen atom, a sulfur atom and a nitrogen atom including, for example, a pyridyl group, a pyridine-N-oxide group, a pyrimidinyl group, a furyl group, a tetrahydrofuryl group, a thienyl group, a tetrahydrothienyl group, a tetrahydropyranyl group, a tetrahydrothiopyranyl group, an oxazolyl group, an isooxazolyl group, an oxadiazolyl group, a thiazolyl group, an isothiazolyl group, a thiadiazolyl group, an imidazolyl group, a triazolyl group and a pyrazolyl group. "A condensed ring" includes, for example, naphthalene, tetrahydronaphthalene, indene, indane, quinoline, quinazoline, indole, indoline, chroman, isochroman, benzodioxane, benzodioxole, benzofuran, dihydrobenzofuran, benzothiophene, dihydrobenzothiophene, benzoxazole, benzothiazole, benzimidazole and indazole.

In the general formula (I) for a substituted pyrazinecarboxanilide derivative, the general formula (II) for a substituted aniline derivative and the general formula (III') for a substituted pyrazinecarboxylic acid derivative of the present invention, $R^1$ is preferably a hydrogen atom, a $C_1$-$C_6$ alkyl group, a halo $C_1$-$C_6$ alkyl group, a $C_1$-$C_6$ alkylcarbonyl group, a halo $C_1$-$C_6$ alkylcarbonyl group, a $C_1$-$C_6$ alkoxycarbonyl group, a halo $C_1$-$C_6$ alkoxycarbonyl group, a $C_1$-$C_6$ alkylcarbonyl $C_1$-$C_6$ alkyl group, a $C_2$-$C_6$ alkenyl group, a halo $C_2$-$C_6$ alkenyl group, a $C_2$-$C_6$ alkynyl group, a halo $C_2$-$C_6$ alkynyl group, a $C_1$-$C_6$ alkoxy $C_1$-$C_6$ alkyl group, a halo $C_1$-$C_6$ alkoxy $C_1$-$C_6$ alkyl group or a $C_1$-$C_6$ alkoxy $C_1$-$C_6$ alkoxy $C_1$-$C_6$ alkyl group and further preferably, a hydrogen atom, a $C_1$-$C_6$ alkyl group, a $C_1$-$C_6$ alkoxy $C_1$-$C_6$ alkyl group, a $C_1$-$C_6$ alkylcarbonyl group or a $C_1$-$C_6$ alkoxycarbonyl group.

$R^2$ is preferably a hydrogen atom, a halogen atom, a $C_1$-$C_6$ alkyl group, a halo $C_1$-$C_6$ alkyl group, a hydroxyl group, a $C_1$-$C_6$ alkoxy group, a halo $C_1$-$C_6$ alkoxy group, a $C_1$-$C_6$ alkoxy $C_1$-$C_3$ alkoxy group or a halo $C_1$-$C_6$ alkoxy $C_1$-$C_3$ alkoxy group, and further preferably, a hydrogen atom, a halogen atom or a $C_1$-$C_6$ alkoxyl group.

G is preferably a $C_2$-$C_{10}$ alkyl group, a halo $C_2$-$C_{10}$ alkyl group, a $C_3$-$C_{10}$ cycloalkyl group or a $C_3$-$C_8$ cycloalkyl $C_1$-$C_6$ alkyl group, and particularly preferably, a $C_2$-$C_{10}$ alkyl group or a $C_3$-$C_8$ cycloalkyl $C_1$-$C_6$ alkyl group.

X is particularly preferably a hydrogen atom. Y is preferably a halogen atom, a $C_1$-$C_6$ alkyl group, a halo $C_1$-$C_6$ alkyl group, a $C_1$-$C_6$ alkoxyl group or a halo $C_1$-$C_6$ alkoxyl group, and particularly preferably, a $C_1$-$C_6$ alkyl group or a halo $C_1$-$C_6$ alkyl group. Preferable m value is 1 or 2 and particularly preferably 1. Z is preferably an oxygen atom.

A salt of a substituted pyrazinecarboxanilide derivative represented by the general formula (I) or a substituted pyrazinecarboxylic acid derivative represented by the general formula (III'), as an intermediate thereof, of the present invention includes a salt of an alkali metal (lithium, sodium, potassium, etc.); a salt of an alkaline earth metal (calcium, magnesium, etc.); an ammonium salt; and a salt or an acid addition salt of an organic amine (methylamine, triethylamine, diethanolamine, piperidine, pyridine, etc.), and the acid addition salt includes, for example, a carboxylate such as acetate, propionate, oxalate, trifluoroacetate and benzoate; a sulfonate such as methanesulfonate, trifluoromethanesulfonate and p-toluenesulfonate; an inorganic acid salt such as a hydrochloride, a sulfate, a nitrate and a carbonate.

A salt of a substituted aniline derivative represented by the general formula (II) is preferably an acid addition salt including, for example, a carboxylate such as acetate, propionate, oxalate, trifluoroacetate and benzoate; a sulfonate such as methanesulfonate, trifluoromethanesulfonate and p-toluenesulfonate; an inorganic acid salt such as a hydrochloride, a sulfate, a nitrate and a carbonate.

A substituted pyrazinecarboxanilide derivative represented by the general formula (I) or an intermediate thereof, i.e. a substituted aniline derivative represented by the general formula (II), of the present invention may contain one or plural numbers of asymmetric centers in the structural formula, and further two or more optical isomers and diastereomers may be present. Consequently, the present invention includes each optical isomer and the mixtures with any ratio thereof. In addition, a substituted pyrazinecarboxanilide derivative represented by the general formula (I) of the present invention may have two types of geometric isomers derived from a C—C double bond in the structure. The present invention includes all of geometric isomers and the mixtures containing them in any ratio.

Representative production methods for a substituted pyrazinecarboxanilide derivative represented by the general formula (I), a substituted aniline derivative represented by the general formula (II), as an intermediate thereof, or a substituted pyrazinecarboxylic acid derivative represented by the general formula (III) are illustrated hereinbelow, but the present invention should not be limited thereto.

Production method 1

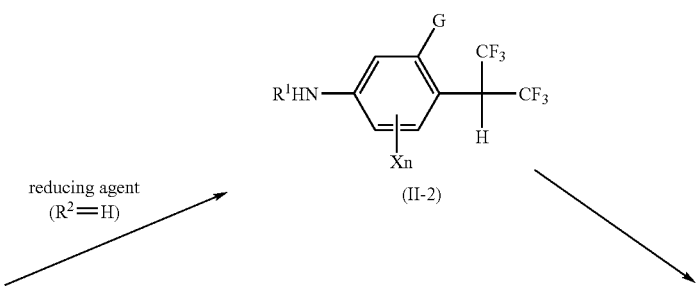

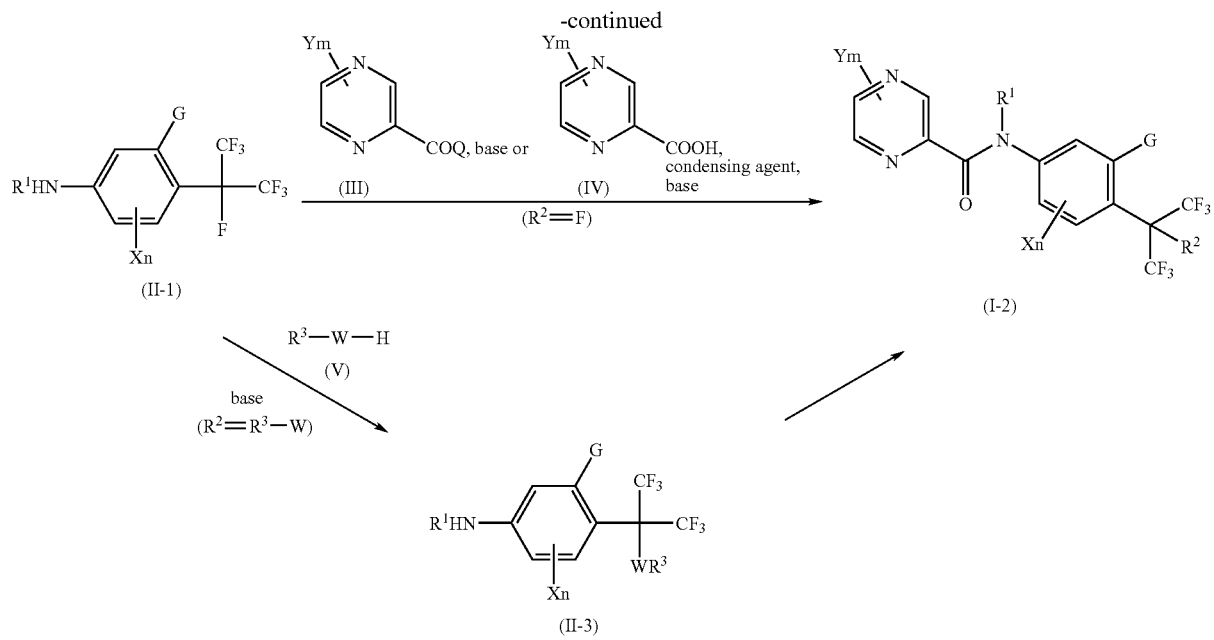

(wherein G, $R^1$, $R^2$, X, n, Y and m are the same as mentioned above; and $R^3$ represents a hydrogen atom, a $C_1$-$C_6$ alkyl group, a halo $C_1$-$C_6$ alkyl group, a phenyl group, a substituted phenyl group or a phenyl $C_1$-$C_4$ alkyl group; W represents —O—, —S— or —N($R^4$)—, wherein $R^4$ represents a hydrogen atom, a $C_1$-$C_6$ alkyl group, a halo $C_1$-$C_6$ alkyl group, a phenyl group, a substituted phenyl group or a phenyl $C_1$-$C_4$ alkyl group; and Q represents a halogen atom or a $C_1$-$C_6$ alkoxyl group)

Among a substituted pyrazinecarboxanilide derivative represented by the general formula (I), a substituted pyrazinecarboxanilide derivative (1-2) wherein Z is represented by 0 can be produced by a reaction of an aniline derivative represented by the general formulas (II-1) to (II-3) with a pyrazinecarboxylic acid halide or a pyrazinecarboxylate ester represented by the general formula (III) in the presence or absence of a base in an inert solvent, or by a reaction of an aniline derivative represented by the general formulas (II-1) to (II-3) with a pyrazinecarboxylic acid represented by the general formula (IV) in the presence of a condensation agent, in the presence or absence of a base, in an inert solvent, however, any usual production methods for amides can also be used.

An aniline derivative represented by the general formula (II-2) can be produced by reducing an aniline derivative represented by the general formula (II-1) in the presence of a reducing agent, in an inert solvent.

An aniline derivative represented by the general formula (II-3) can be produced by a reaction of an aniline derivative represented by the general formula (II-1) with an alcohol derivative, a thiol derivative or an amine derivative represented by the general formulas (V), in the presence or absence of a base in an inert solvent.

From the General Formula (II-1) to the General Formula (II-2)

An Example of a Reducing Agent Used in the present reaction includes metal hydrides such as lithium aluminum hydride, lithium borohydride, sodium borohydride, diisobutyl aluminium hydride and sodium bis(2-methoxyethoxy) aluminium hydride, metal such as lithium or metal salts. The amount used is selected, as appropriate, in the range from equivalent to excess amount relative to an aniline derivative represented by the general formula (II-1).

An example of an inert solvent used in the present reaction, which may be any one as long as it does not significantly inhibit progress of the present reaction, includes aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight chain or cyclic ethers such as diethyl ether, dioxane and tetrahydrofuran, and these inert solvents can be used alone or in combination of two or more kinds.

Reaction temperature is in the range from room temperature to boiling temperature of an inert solvent used and reaction time may be in the range from several minutes to 50 hours, although it depends on reaction scale and reaction temperature.

After completion of the reaction, desired compound may be isolated from the reaction mixture by a conventional method and the desired compound can be produced by purification using recrystallization or column chromatography, etc, if necessary. The desired compound may also be subjected to subsequent reaction step without isolation from the reaction mixture.

From the General Formula (II-1) to the General Formula (II-3)

An example of a base used in the present reaction includes metal hydrides such as lithium hydride, sodium hydride and potassium hydride; metal alcoholates such as sodium methoxide, sodium ethoxide and potassium tert-butoxide; and alkyl metals such as n-butyl lithium, sec-butyl lithium and tert-butyl lithium. The amount used is selected, as appropriate, in the range from equivalent to excess amount relative to an aniline derivative represented by the general formula (II-1).

As an example of an inert solvent used in the present reaction, which may be any one as long as it does not significantly inhibit progress of the present reaction, includes aromatic hydrocarbons such as benzene, toluene and xylene; alcohols such as methanol and ethanol; straight chain or cyclic ethers such as diethyl ether, 1,2-dimethoxyethane, dioxane and tetrahydrofuran, and these inert solvents can be used alone or in combination of two or more kinds.

Reaction temperature is in the range from −70° C. to boiling temperature of an inert solvent used and reaction time may be in the range from several minutes to 50 hours, although it depends on reaction scale and reaction temperature.

After completion of the reaction, desired compound may be isolated from the reaction mixture by a conventional method and the desired compound can be produced by purification using recrystallization or column chromatography, etc, if necessary. The desired compound may also be subjected to subsequent reaction step without isolation from the reaction mixture.

From the General Formula (II-1), (II-2) or (II-3) to the General Formula (I-2)

An example of a condensation agent used in the present reaction includes diethyl cyanophosphate (DEPC), carbonyldiimidazole (CDI), 1,3-dicyclohexylcarbodiimide (DCC), chloroformates and 2-chloro-1-methylpyridinium iodide.

As a base used in the present reaction, an inorganic base or an organic base is included and an example of an inorganic base includes alkali metal hydroxides such as sodium hydroxide and potassium hydroxide; alkali metal hydrides such as sodium hydride and potassium hydride; alkali metal salts of alcohol such as sodium ethoxide and potassium tert-butoxide; carbonates such as sodium carbonate, potassium carbonate and sodium hydrogen carbonate; and organic bases such as triethylamine, pyridine and DBU, and the amount used is selected, as appropriate, in the range from equivalent to excess amount relative to a pyrazinecarboxylic acid derivative represented by the general formula (III) or (IV).

An example of an inert solvent used in the present reaction, which may be any one as long as it does not significantly inhibit progress of the present reaction, includes aromatic hydrocarbons such as benzene, toluene and xylene; halogenated hydrocarbons such as methylene chloride, chloroform and carbon tetrachloride; halogenated aromatic hydrocarbons such as chlorobenzene, dichlorobenzene; chain or cyclic ethers such as diethyl ether, dioxane and tetrahydrofuran; esters such as ethyl acetate; amides such as dimethylformamide and dimethylacetamide; dimethylsulfoxide, 1,3-dimethyl-2-imidazolidinone, acetone and methyl ethyl ketone, and these inert solvents can be used alone or in combination of two or more kinds.

As the present reaction is an equimolar reaction, each reactant may be used in equal mole, however, any of the reactants may also be used in excess. Reaction temperature is in the range from room temperature to boiling temperature of an inert solvent used and reaction time may be in the range from several minutes to 48 hours, although it depends on reaction scale and reaction temperature.

After completion of the reaction, desired compound may be isolated from the reaction mixture by a conventional method and the desired compound can be produced by purification using recrystallization or column chromatography, etc, if necessary.

An aniline derivative represented by the general formula (II-1), as a raw material of the present reaction, can be produced in accordance with a method disclosed in JP-A-11-302233 or JP-A-2001-122836.

A pyrazinecarboxylic acid derivative represented by the general formulas (III), (III') or (IV) can be produced in accordance with several methods described in known literatures (for example, Journal of Organic Chemistry Vol. 67, 556-565 (2002); Journal of American Chemical Society, Vol. 70, 3911 (1948); Chemical & Pharmaceutical Bulletin, 20 (10), 2204-2208 (1970); Journal of Heterocyclic Chemistry, Vol. 34, 27 (1997); Synthesis, 923-924 (1990); WO 2001/070708; Tetrahedron Letters, Vol. 32, No. 52, 7689-7690 (1991); and Journal of American Chemical Society, Vol. 68, 400 (1946)).

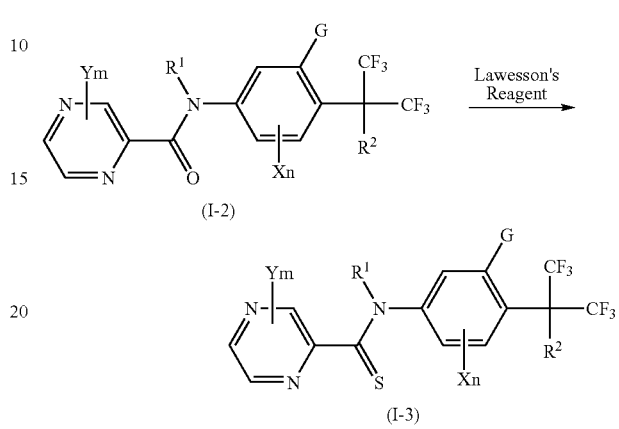

(wherein $R^1$, $R^2$, G, X, Y, m and n are the same mentioned above).

Among substituted pyrazinecarboxanilide derivatives represented by the general formula (I), a substituted pyrazinecarboxanilide derivative (I-3) wherein Z is represented by S can be produced by a reaction of an aniline derivative represented by (I-2) with Lawesson's Reagent in accordance with a known method (Tetrahedron Lett., 21 (42), 4061 (1980)).

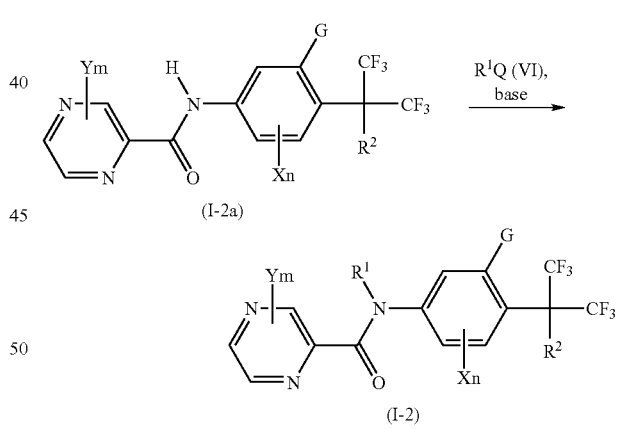

(wherein $R^1$, $R^2$, G, X, Y, Q, m and n are the same mentioned above).

Among substituted pyrazinecarboxanilide derivatives represented by the general formula (I), a substituted pyrazinecarboxanilide derivative (I-2) wherein $R^1$ is other than a hydrogen atom can be produced by a reaction of an amide derivative represented by the general formula (I-2a) with a halide derivative or an ester derivative represented by the general formula (VI), in the presence or absence of a base, in an inert solvent.

As an example of a base used in the present reaction includes metal hydrides such as lithium hydride, sodium hydride and potassium hydride; metal alcoholates such as sodium methoxide, sodium ethoxide and potassium tert-butoxide; alkyl metals such as n-butyl lithium, sec-butyl lithium and tert-butyl lithium, and the amount used is selected, as appropriate, in the range from equivalent to excess amount relative to an amide derivative represented by the general formula (I-2a).

An example of an inert solvent used in the present reaction, which may be any one as long as it does not significantly inhibit progress of the present reaction, includes aromatic hydrocarbons such as benzene, toluene and xylene; alcohols such as methanol and ethanol; straight chain or cyclic ethers such as diethyl ether, 1,2-dimethoxyethane, dioxane and tetrahydrofuran, and these inert solvents can be used alone or in combination of two or more kinds.

Reaction temperature is in the range from −70° C. to boiling temperature of an inert solvent used and reaction time may be in the range from several minutes to 50 hours, although it depends on reaction scale and reaction temperature.

After completion of the reaction, desired compound may be isolated from the reaction mixture by a conventional method and the desired compound can be produced by purification using recrystallization or column chromatography, etc, if necessary. The desired compound may also be subjected to subsequent reaction step without isolation from the reaction mixture.

Typical compounds of substituted pyrazinecarboxanilide derivatives represented by the general formula (I) are exemplified in Table 1, and typical compounds of substituted aniline derivatives represented by the general formula (II) are exemplified in Table 2, and typical compounds of substituted pyrazinecarboxylic acid derivatives represented by the general formula (III') are exemplified in Table 3, however, the present invention should not be limited to these. In "property" column of Table 1, melting point (° C.) or refractive index ($n_D$(° C.)) is shown and on compounds described as amorphous, $^1$HNMR data thereof were shown in Table 4. In the Tables, "n-" represents normal, and likewise "i-" is iso, "t-" is tertiary, "c-" is cyclo, "Me" is a methyl group, "Et" is an ethyl group, "Pr" is a propyl group, "Bu" is a butyl group, "Ph" is a phenyl group and "Ac" is an acetyl group.

TABLE 1

General formula (I-4)

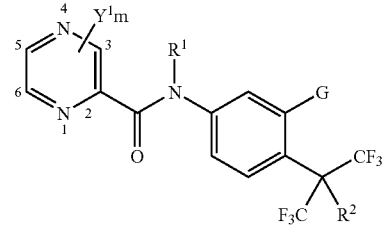

(I-4)

| No. | G | $Y^1m$ | $R^1$ | $R^2$ | Property |
|---|---|---|---|---|---|
| 1-1 | Et | 3-Me | H | H | 59-61 |
| 1-2 | Et | 3-Me | H | OMe | 66-70 |
| 1-3 | Et | 3-Me | H | OEt | 111-112 |
| 1-4 | Et | 3-OMe | H | OMe | 101-102 |
| 1-5 | n-Pr | 3-Me | H | F | 122-123 |
| 1-6 | n-Pr | 3-Me | H | H | 95-98 |
| 1-7 | n-Pr | 3-Me | H | OMe | 111-113 |
| 1-8 | n-Pr | 3-Me | H | OEt | 114-115 |
| 1-9 | n-Pr | 3-Cl | H | H | 100-103 |
| 1-10 | n-Pr | 3-Cl | H | OMe | 129-130.5 |
| 1-11 | n-Pr | 3-Cl | H | OEt | 143-144 |
| 1-12 | n-Pr | 3-OMe | H | H | 112-113 |
| 1-13 | n-Pr | 3-OMe | H | OMe | 144.5-146 |
| 1-14 | n-Pr | 3-CF$_3$ | H | OMe | 99-101 |
| 1-15 | i-Bu | H | H | H | 88-90 |
| 1-16 | i-Bu | 3-Me | H | F | 139.5-141 |
| 1-17 | i-Bu | 3-Me | H | H | 133-134 |
| 1-18 | i-Bu | 3-Me | H | OMe | 118-119 |
| 1-19 | i-Bu | 3-Me | H | OMe | 70-72 |
| 1-20 | i-Bu | 3-Me | H | OEt | amorphous |
| 1-21 | i-Bu | 3-CH$_2$OH | H | OMe | 113-115 |
| 1-22 | i-Bu | 3-CH$_2$OAc | H | H | 52-55 |
| 1-23 | i-Bu | 3-CH$_2$OAc | H | OMe | 75-77 |
| 1-24 | i-Bu | 3-CH$_2$SMe | H | H | 1.5411(20.4) |
| 1-25 | i-Bu | 3-Cl | H | H | 128-129 |
| 1-26 | i-Bu | 3-Cl | H | OMe | 1.5394(23.3) |
| 1-27 | i-Bu | 3-Cl | Et | OMe | 78.9-80.4 |
| 1-28 | i-Bu | 3-OMe | H | H | 135.5-137 |
| 1-29 | i-Bu | 3-OMe | H | OMe | 118-119 |
| 1-30 | i-Bu | 3-OMe | H | OEt | 116-119 |
| 1-31 | i-Bu | 3-OEt | H | H | 119-121 |
| 1-32 | i-Bu | 3-SMe | H | H | 1.5351(26.7) |
| 1-33 | i-Bu | 3-SOMe | H | H | 1.5258(25.9) |
| 1-34 | i-Bu | 3-SO$_2$Me | H | H | 220-222 |
| 1-35 | i-Bu | 3-NMe$_2$ | H | H | 1.5299(20.5) |
| 1-36 | i-Bu | 3-NHPh | H | H | 144-145 |

TABLE 1-continued

General formula (I-4)

| No. | G | Y¹m | R¹ | R² | Property |
|---|---|---|---|---|---|
| 1-37 | i-Bu | 3-(4-Cl—Ph) | H | H | 49.2 |
| 1-38 | i-Bu | 3-C≡CSiMe$_3$ | H | OMe | amorphous |
| 1-39 | i-Bu | 3-CH$_2$F | H | OMe | 1.4829(27.7) |
| 1-40 | i-Bu | 3-CH$_2$F | H | H | |
| 1-41 | i-Bu | 3-CH$_2$F | H | OMe | |
| 1-42 | i-Bu | 3-CF$_3$ | H | H | 1.4825(27.7) |
| 1-43 | i-Bu | 3-CF$_3$ | H | OMe | 129-132 |
| 1-44 | i-Bu | 3-OCF$_3$ | H | H | |
| 1-45 | i-Bu | 3-OCF$_3$ | H | OMe | |
| 1-46 | i-Bu | 3-OCHF$_2$ | H | H | 169.1-171.3 |
| 1-47 | i-Bu | 3-OCHF$_2$ | H | OMe | |
| 1-48 | i-Bu | 3-OCH$_2$CF$_3$ | H | OMe | 151 |
| 1-49 | i-Bu | 3-OCH$_2$CH$_2$OMe | H | OMe | 99-100 |
| 1-50 | i-Bu | 3-OCH$_2$Ph | H | OMe | 74-77 |
| 1-51 | i-Bu | 3-F | H | H | 118-119 |
| 1-52 | i-Bu | 3-F | H | OMe | |
| 1-53 | i-Bu | 3-Br | H | H | 142-144 |
| 1-54 | i-Bu | 3-Br | H | OMe | 1.5440(20.0) |
| 1-55 | i-Bu | 3-I | H | H | |
| 1-56 | i-Bu | 3-I | H | OMe | |
| 1-57 | i-Bu | 3-Et | H | H | |
| 1-58 | i-Bu | 3-Et | H | OMe | |
| 1-59 | i-Bu | 5-Me | H | H | 119-121 |
| 1-60 | i-Bu | 3-Me-5-OH | H | OMe | 186-187 |
| 1-61 | i-Bu | 3-Me-5-OEt | H | OMe | 1.5210(20.6) |
| 1-62 | i-Bu | 3-Me-5-OAc | H | H | 173-173.5 |
| 1-63 | i-Bu | 3-Me-5-OAc | H | OMe | amorphous |
| 1-64 | i-Bu | 3-Me-6-Cl | H | OMe | 143-145 |
| 1-65 | i-Bu | 3-Me-6-OAc | H | OMe | 144-146 |
| 1-66 | i-Bu | 3,5-Me$_2$ | H | H | |
| 1-67 | i-Bu | 3,5-Me$_2$ | H | OMe | |
| 1-68 | i-Bu | 3,6-Me$_2$ | H | H | 135-137 |
| 1-69 | i-Bu | 3,6-Me$_2$ | H | OMe | 127-128 |
| 1-70 | i-Bu | 3,6-Me$_2$-5-Cl | H | H | 120-121 |
| 1-71 | i-Bu | 3,6-Me$_2$-5-OMe | H | H | 155-158 |
| 1-72 | i-Bu | 3,5,6-Me$_3$ | H | H | 98-100 |
| 1-73 | CH=CMe$_2$ | 3-Me | H | OMe | 94-97 |
| 1-74 | CHBrCHMe$_2$ | 3-Me | H | H | 181-181.5 |
| 1-75 | CHBrCHMe$_2$ | 3-Me | H | OMe | 148-151 |
| 1-76 | n-Bu | 3-Me | H | H | 84-87 |
| 1-77 | n-Bu | 3-Me | H | OMe | 87-89.5 |
| 1-78 | (CH$_2$)$_4$Me | 3-Me | H | H | 1.5245(24.6) |
| 1-79 | CH$_2$CH$_2$CHMe$_2$ | 3-Me | H | H | 77-78 |
| 1-80 | CH$_2$CH$_2$CHMe$_2$ | 3-Me | H | OMe | 110-112 |
| 1-81 | CH$_2$CH(Me)Et | 3-Me | H | H | 81-83 |
| 1-82 | CH$_2$CH(Me)Et | 3-Me | H | OMe | 92-94 |
| 1-83 | CH$_2$CHEt$_2$ | 3-Me | H | H | |
| 1-84 | CH$_2$CHEt$_2$ | 3-Me | H | OMe | |
| 1-85 | CH(Me)CH$_2$CHMe$_2$ | 3-Me | H | H | |
| 1-86 | CH(Me)CH$_2$CHMe$_2$ | 3-Me | H | OMe | |
| 1-87 | CH$_2$-c-C$_5$H$_9$ | 3-Me | H | H | 110-112 |
| 1-88 | CH$_2$-c-C$_5$H$_9$ | 3-Me | H | OMe | 113-114 |
| 1-89 | CH$_2$-c-C$_6$H$_{11}$ | 3-Me | H | H | 67-70 |
| 1-90 | Bn | 3-Me | H | H | 103-105 |
| 1-91 | i-Bu | 3-Me | Me | OMe | |
| 1-92 | i-Bu | 3-Me | i-Pr | OMe | |
| 1-93 | i-Bu | 3-Me | CH$_2$CH=CH$_2$ | OMe | |
| 1-94 | i-Bu | 3-Me | CH$_2$C≡CH | OMe | |
| 1-95 | i-Bu | 3-Me | CH$_2$Ph | OMe | |
| 1-96 | i-Bu | 3-Me | COO-i-Bu | OMe | 1.4814(23.2) |
| 1-97 | i-Bu | 3-Me | COO-i-Bu | H | |
| 1-98 | i-Bu | 3-Me | COO-t-Bu | OMe | 1.4850(23.8) |
| 1-99 | i-Bu | 3-Me | COO-t-Bu | H | |

TABLE 1-continued

General formula (I-4)

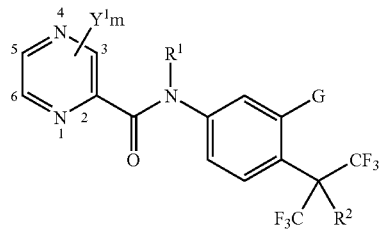

(I-4)

| No. | G | Y$^1$m | R$^1$ | R$^2$ | Property |
|---|---|---|---|---|---|
| 1-100 | i-Bu | 3-Me | COO(CH$_2$)$_3$Cl | OMe | |
| 1-101 | i-Bu | 3-Me | COO(CH$_2$)$_3$Cl | H | |
| 1-102 | i-Bu | 3-Me | COOCH$_2$-t-Bu | OMe | |
| 1-103 | i-Bu | 3-Me | COOCH$_2$-t-Bu | H | |
| 1-104 | i-Bu | 3-Me | COOCH$_2$CCl$_3$ | OMe | 1.5038(22.0) |
| 1-105 | i-Bu | 3-Me | COOCH$_2$CCl$_3$ | H | |
| 1-106 | i-Bu | 3-Me | Ac | OMe | 1.4955(23.0) |
| 1-107 | i-Bu | 3-Me | Ac | H | |
| 1-108 | i-Bu | 3-Me | COCF$_3$ | OMe | |
| 1-109 | i-Bu | 3-Me | COCF$_3$ | H | |
| 1-110 | i-Bu | 3-Me | COEt | OMe | |
| 1-111 | i-Bu | 3-Me | COEt | H | |
| 1-112 | i-Bu | 3-Me | CH$_2$COOEt | OMe | 119 |
| 1-113 | i-Bu | 3-Me | CH$_2$COOEt | H | |
| 1-114 | i-Bu | 3-Me | CH$_2$OEt | OMe | 1.4899(23.9) |
| 1-115 | i-Bu | 3-Me | CH$_2$OEt | H | |
| 1-116 | i-Bu | 3-Me | CH$_2$OCH$_2$OEt | OMe | |
| 1-117 | i-Bu | 3-Me | CH$_2$OCH$_2$Ph | OMe | 1.5206(22.0) |
| 1-118 | i-Bu | 3-Me | CH$_2$SMe | OMe | |
| 1-119 | i-Bu | 3-Me | CH$_2$SMe | H | |
| 1-120 | i-Bu | 3-Me | CH$_2$CN | OMe | amorphous |
| 1-121 | i-Bu | 3-Me | CH$_2$CN | H | amorphous |
| 1-122 | i-Bu | 3-CF$_3$ | Me | H | |
| 1-123 | i-Bu | 3-CF$_3$ | i-Pr | H | |
| 1-124 | i-Bu | 3-CF$_3$ | CH$_2$CH=CH$_2$ | H | |
| 1-125 | i-Bu | 3-CF$_3$ | CH$_2$C≡CH | H | 1.4680(23.5) |
| 1-126 | i-Bu | 3-CF$_3$ | CH$_2$Ph | H | |
| 1-127 | i-Bu | 3-CF$_3$ | COO-i-Bu | OMe | 1.4720(23.5) |
| 1-128 | i-Bu | 3-CF$_3$ | COO-i-Bu | H | 88-89 |
| 1-129 | i-Bu | 3-CF$_3$ | COO-t-Bu | OMe | 1.4690(24.0) |
| 1-130 | i-Bu | 3-CF$_3$ | COO-t-Bu | H | |
| 1-131 | i-Bu | 3-CF$_3$ | COO(CH$_2$)$_3$Cl | OMe | |
| 1-132 | i-Bu | 3-CF$_3$ | COO(CH$_2$)$_3$Cl | H | |
| 1-133 | i-Bu | 3-CF$_3$ | COOCH$_2$-t-Bu | OMe | |
| 1-134 | i-Bu | 3-CF$_3$ | COOCH$_2$-t-Bu | H | 122-124 |
| 1-135 | i-Bu | 3-CF$_3$ | COOCH$_2$CCl$_3$ | OMe | 1.4811(24.1) |
| 1-136 | i-Bu | 3-CF$_3$ | COOCH$_2$CCl$_3$ | H | 1.4790(24.2) |
| 1-137 | i-Bu | 3-CF$_3$ | Ac | OMe | 1.4770(25.3) |
| 1-138 | i-Bu | 3-CF$_3$ | Ac | H | 1.4620(24.7) |
| 1-139 | i-Bu | 3-CF$_3$ | COCF$_3$ | OMe | |
| 1-140 | i-Bu | 3-CF$_3$ | COCF$_3$ | H | |
| 1-141 | i-Bu | 3-CF$_3$ | CO-n-Bu | OMe | |
| 1-142 | i-Bu | 3-CF$_3$ | CO-n-Bu | H | |
| 1-143 | i-Bu | 3-CF$_3$ | CH$_2$COOEt | OMe | |
| 1-144 | i-Bu | 3-CF$_3$ | CH$_2$COOEt | H | |
| 1-145 | i-Bu | 3-CF$_3$ | CH$_2$OEt | OMe | 1.4730(24.2) |
| 1-146 | i-Bu | 3-CF$_3$ | CH$_2$OEt | H | 1.4650(23.5) |
| 1-147 | i-Bu | 3-CF$_3$ | CH$_2$OCH$_2$OEt | OMe | |
| 1-148 | i-Bu | 3-CF$_3$ | CH$_2$OCH$_2$OEt | H | |
| 1-149 | i-Bu | 3-CF$_3$ | CH$_2$SMe | OMe | |
| 1-150 | i-Bu | 3-CF$_3$ | CH$_2$SMe | H | |
| 1-151 | i-Bu | 3-CF$_3$ | CH$_2$CN | OMe | |
| 1-152 | i-Bu | 3-CF$_3$ | CH$_2$CN | H | |
| 1-153 | i-Bu | 3-CF$_3$ | COOMe | H | 1.4715(23.8) |
| 1-154 | i-Bu | 3-CF$_3$ | COOEt | OMe | 1.4698(24.9) |
| 1-155 | i-Bu | 3-CF$_3$ | COO-n-Bu | OMe | 1.4700(24.4) |
| 1-156 | i-Bu | 3-CF$_3$ | COOCH$_2$CH$_2$OMe | OMe | 1.4724(24.5) |
| 1-157 | i-Bu | 3-CF$_3$ | CH$_2$OMe | OMe | 93-94 |
| 1-158 | i-Bu | 3-CF$_3$ | COEt | OMe | 1.4765(25.2) |
| 1-159 | i-Bu | 3-Cl | CH$_2$OEt | OMe | 1.4965(22.2) |
| 1-160 | i-Bu | 3-Cl | CH$_2$OEt | H | 1.4968(20.4) |
| 1-161 | i-Bu | 3-Cl | COOCH$_2$-t-Bu | OMe | |
| 1-162 | i-Bu | 3-Cl | COOCH$_2$-t-Bu | H | |

TABLE 1-continued

General formula (I-4)

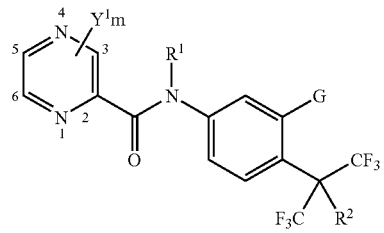

| No. | G | $Y^1m$ | $R^1$ | $R^2$ | Property |
|---|---|---|---|---|---|
| 1-163 | i-Bu | 3-OMe | CH$_2$OEt | OMe | 96.3-99.1 |
| 1-164 | i-Bu | 3-OMe | CH$_2$OEt | H | |
| 1-165 | i-Bu | 3-OMe | COOCH$_2$t-Bu | OMe | |
| 1-166 | i-Bu | 3-OMe | COOCH$_2$t-Bu | H | |
| 1-167 | i-Bu | 3-OCF$_3$ | CH$_2$OEt | OMe | |
| 1-168 | i-Bu | 3-OCF$_3$ | COOCH$_2$-t-Bu | H | |
| 1-169 | i-Bu | 3-OCF$_3$ | Ac | OMe | |
| 1-170 | i-Bu | 3-OCHF$_2$ | CH$_2$OCH$_2$Ph | OMe | |
| 1-171 | i-Bu | 3-OCHF$_2$ | COO-t-Bu | H | |
| 1-172 | i-Bu | 3-OCHF$_2$ | COEt | OMe | |
| 1-173 | i-Bu | 3-CHF$_2$ | CH$_2$OCH$_2$OEt | H | |
| 1-174 | i-Bu | 3-CHF$_2$ | COO(CH$_2$)$_3$Cl | OMe | |
| 1-175 | i-Bu | 3-CHF$_2$ | CO$_2$-t-Bu | H | |
| 1-176 | i-Bu | 3-CN | CH$_2$OEt | OMe | |
| 1-177 | i-Bu | 3-CN | Ac | H | |
| 1-178 | i-Bu | 3-COOMe | CH$_2$OEt | OMe | |
| 1-179 | i-Bu | 3-COOMe | H | H | 118-120 |
| 1-180 | i-Bu | 3-COOH | H | H | 154-157 |
| 1-181 | i-Bu | 3-NO$_2$ | H | OMe | |
| 1-182 | i-Bu | 3-NO$_2$ | H | H | |
| 1-183 | i-Bu | 3-C≡CH | H | OMe | |
| 1-184 | i-Bu | H | Et | OMe | 70-72 |
| 1-185 | CH$_2$CH$_2$CHMe$_2$ | 3-Me | H | F | 109-110 |
| 1-186 | Et | 3-Me | H | F | 75-77 |
| 1-187 | i-Pr | 3-Me | H | F | 149-150 |
| 1-188 | i-Bu | 3-Me | SN(n-Bu)$_2$ | OMe | |
| 1-189 | i-Bu | 3-Me | SN(n-Bu)$_2$ | H | 1.5029(22.4) |
| 1-190 | i-Bu | 3-Me | SN(Me)COO-n-Bu | OMe | |
| 1-191 | i-Bu | 3-Me | SN(Me)COO-n-Bu | H | |
| 1-192 | i-Bu | 3-Me | SN(i-Pr)CH$_2$CH$_2$COOEt | OMe | |
| 1-193 | i-Bu | 3-Me | SN(i-Pr)CH$_2$CH$_2$COOEt | H | |
| 1-194 | i-Bu | 3-Me | PS(OMe)$_2$ | OMe | |
| 1-195 | i-Bu | 3-Me | PO(OMe)$_2$ | OMe | |
| 1-196 | i-Bu | 3-OMe | H | F | 119-121 |
| 1-197 | Et | 3-OMe | H | F | 1.5272(25.2) |
| 1-198 | i-Bu | 3-Me-5-Cl | H | H | 100-104 |
| 1-199 | i-Bu | 3-CF$_3$ | COSMe | H | 1.4824(24.7) |
| 1-200 | i-Bu | 3-CF$_3$ | COSMe | OMe | 1.4925(24.7 |
| 1-201 | i-Bu | 3-CF$_3$ | COSEt | H | 105-106 |
| 1-202 | i-Bu | 3-CF$_3$ | COSEt | OMe | 1.4880(24.6) |
| 1-203 | i-Bu | 3-CF$_3$ | COOMe | OMe | 1.4775(22.4) |
| 1-204 | i-Bu | 3-CF$_3$ | COOEt | H | 1.4638(23.2) |
| 1-205 | i-Bu | 3-CF$_3$ | COOCH$_2$CH=CH$_2$ | H | 1.4675(23.2) |
| 1-206 | i-Bu | 3-CF$_3$ | COOCH$_2$CH=CH$_2$ | OMe | 1.4751(23.2) |
| 1-207 | i-Bu | 3-CF$_3$ | COO-n-Pr | H | 1.4649(23.0) |
| 1-208 | i-Bu | 3-CF$_3$ | COO-n-Pr | OMe | 1.4700(24.2) |
| 1-209 | i-Bu | 3-CF$_3$ | COOCH$_2$Cl | OMe | 1.4805(24.0) |
| 1-210 | i-Bu | 3-CF$_3$ | COOCH$_2$CH$_2$OMe | H | 86-88 |
| 1-211 | i-Bu | 3-CF$_3$ | COOPh | OMe | 1.4850(24.2) |
| 1-212 | i-Bu | 3-CF$_3$ | COOCH$_2$Ph | OMe | 1.4868(23.4) |
| 1-213 | i-Bu | 3-CF$_3$ | CH$_2$OMe | H | 1.4670(23.1) |
| 1-214 | i-Bu | 3-CF$_3$ | CH$_2$OCH$_2$Ph | H | 1.4895(23.1) |
| 1-215 | i-Bu | 3-CF$_3$ | CH$_2$OCH$_2$CH$_2$OMe | H | 1.4730(24.8) |
| 1-216 | i-Bu | 3-CF$_3$ | CH$_2$OCH$_2$CH$_2$OMe | OMe | 1.4739(23.2) |
| 1-217 | i-Bu | 3-CF$_3$ | COEt | H | 87-88 |
| 1-218 | i-Bu | 3-CF$_3$ | CO-n-Pr | H | 85-86 |
| 1-219 | i-Bu | 3-CF$_3$ | CO-c-Pr | H | 1.4760(23.2) |
| 1-220 | i-Bu | 3-CF$_3$ | CO-i-Pr | H | 111-113 |
| 1-221 | i-Bu | 3-CF$_3$ | CO-i-Bu | H | 113-114 |
| 1-222 | i-Bu | 3-CF$_3$ | COCH$_2$OAc | H | 158-159 |
| 1-223 | i-Bu | 3-CHCl$_2$ | H | H | 89-91 |
| 1-224 | i-Bu | 3-OCHF$_2$ | CH$_2$OEt | H | 1.4709(26.2) |

TABLE 1-continued

General formula (I-4)

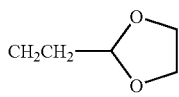

| No. | G | $Y^1m$ | $R^1$ | $R^2$ | Property |
|---|---|---|---|---|---|
| 1-225 | i-Bu | 3-Me | CH$_2$CH$_2$-[1,3-dioxolan-2-yl] | OMe | 1.5030(22.6) |
| 1-226 | n-Pr | 3-CF$_3$ | COOMe | OMe | 1.4789(21.7) |
| 1-227 | n-Pr | 3-CF$_3$ | COOEt | OMe | 1.4770(21.8) |
| 1-228 | n-Pr | 3-CF$_3$ | CH$_2$OMe | OMe | 1.4760(21.8) |
| 1-229 | n-Pr | 3-CF$_3$ | Ch$_2$OEt | OMe | 1.4760(21.8) |
| 1-230 | n-Pr | 3-CF$_3$ | CO-c-Pr | OMe | 1.4910(21.8) |

TABLE 2

General formula (II-4)

(II-4)

| No | G | $R^1$ | $R^2$ | $^1$H-NMR[CDCl$_3$/TMS, δ(ppm)] |
|---|---|---|---|---|
| 2-1 | Et | H | F | 7.22(d, 1H), 6.60-6.49(m, 2H), 3.83(bs,2H), 2.73(m, 2H), 1.20(m, 3H) |
| 2-2 | Et | H | H | 7.30(d, 1H), 6.58-6.53(m, 2H), 4.30(m, 1H), 3.73(bs, 2H), 2.58(dd, 2H), 1.20(t, 3H) |
| 2-3 | Et | H | OMe | 7.23(d, 1H), 6.69(d, 1H), 6.53(dd, 1H), 4.00-3.70(br, 2H), 3.41(s, 3H), 2.93(dd, 2H), 1.23(t, 3H) |
| 2-4 | Et | H | OEt | 7.22(d, 1H), 6.70(s, 1H), 6.54(d, 1H), 3.80(br, 2H), 3.71(dd, 2H), 2.93(dd, 2H), 1.29(t, 3H), 1.21(t, 3H) |
| 2-5 | n-Pr | H | F | 7.22(d, 1H), 6.58-6.50(m, 2H), 4.00-3.70(br, 2H), 2.65(m, 2H), 1.58(m, 2H), 0.97(t, 3H) |
| 2-6 | n-Pr | H | H | 7.31(d, 1H), 6.59-6.54(m, 2H), 4.29(m, 1H), 3.79(bs,2H), 2.52(t, 2H), 1.57(m, 2H), 0.99(t, 3H) |
| 2-7 | n-Pr | H | OMe | 7.23(d, 1H), 6.67(d, 1H), 6.52(d, 1H), 3.78(bs, 2H), 3.42(s, 3H), 2.85(m, 2H), 1.62(m, 2H), 1.00(t, 3H) |
| 2-8 | n-Pr | H | OEt | 7.22(d, 1H), 6.66(d, 1H), 6.51(dd, 1H), 3.77(bs, 2H), 3.59(dd, 2H), 2.86(m, 2H), 1.61 (m, 2H), 1.29(t, 3H), 1.01(t, 3H) |
| 2-9 | i-Bu | H | F | 7.23(d, 1H), 6.54(dt, 1H), 6.51(d, 1H), 3.90 (bs, 2H), 2.55(dd, 2H), 1.83(m, 1H), 0.91 (d, 6H) |
| 2-10 | i-Bu | H | OMe | 7.25(d, 1H), 6.71(d, 1H), 6.54(dd, 1H), 3.78 (bs, 2H), 3.43(s, 3H), 2.81(d, 2H), 2.13 (m, 1H), 0.92(d, 6H) |
| 2-11 | i-Bu | H | OEt | 7.25(d, 1H), 6.70(d, 1H), 6.52(dd, 1H), 4.18(br, 2H), 3.59(dd, 2H), 2.82(d, 2H), 2.14 (m, 1H), 1.30(t, 3H), 0.90(d, 6H) |
| 2-12 | i-Bu | Et | OMe | 7.27(d, 1H), 6.61(d, 1H), 6.45(dd, 1H), 3.74(br, 1H), 3.43(s, 3H), 3.17(dd, 2H), 2.82 (d, 2H), 2.39(m, 1H), 1.26(t, 3H), 0.93 (d, 6H) |

TABLE 2-continued

General formula (II-4)

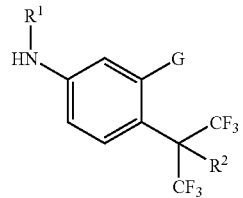

(II-4)

| No | G | R¹ | R² | ¹H-NMR[CDCl₃/TMS, δ(ppm)] |
|---|---|---|---|---|
| 2-13 | i-Bu | H | H | 7.30(d, 1H), 6.57(dd, 1H), 6.50(d, 1H), 4.28 (m, 1H), 3.80(bs, 2H), 2.41(d, 2H), 1.78 (m, 1H), 0.91(d, 6H) |
| 2-14 | n-Bu | H | H | 7.22(d, 1H), 6.60-6.50(m, 2H), 4.29(m, 1H), 3.87(bs, 2H), 2.54(m, 2H), 1.53(m, 2H), 1.39(m, 2H), 0.95(t, 3H) |
| 2-15 | n-Bu | H | F | 7.30(d, 1H), 6.56-6.49(m, 2H), 4.00(br, 2H), 2.66(m, 2H), 1.54(m, 2H), 1.39(m, 2H), 0.92(t, 3H) |
| 2-16 | n-Bu | H | OMe | 7.30(d, 1H), 6.68(d, 1H), 6.52(dd, 1H), 3.78(br, 2H), 3.41(s, 3H), 2.88(m, 2H), 1.58 (m, 2H), 1.42(m, 2H), 0.95(t, 3H) |
| 2-17 | (CH₂)₄Me | H | F | 7.22(d, 1H), 6.55-6.50(m, 2H), 3.83(bs, 2H), 2.66(m, 2H), 1.56(m, 2H), 1.32(m, 4H), 0.89(t, 3H) |
| 2-18 | (CH₂)₄Me | H | H | 7.30(d, 1H), 6.58-6.53(m, 2H), 4.28(m, 1H), 4.03(bs, 2H), 2.53(t, 2H), 1.54(m, 2H), 1.34(m, 4H), 0.90(t, 3H) |
| 2-19 | CH₂CH(Me)Et | H | F | 7.23(d, 1H), 6.60-6.48(m, 2H), 3.83(br, 2H), 2.74(m, 1H), 2.41(m, 1H), 1.61(m, 1H), 1.41(m, 1H), 1.18(m, 1H), 0.90(t, 3H), 0.85(d, 3H) |
| 2-20 | CH₂CH(Me)Et | H | OMe | 7.31(d, 1H), 6.72(d, 1H), 6.53(dd, 1H), 3.80(br, 2H), 3.43(s, 3H), 2.85(m, 2H), 1.89(m, 1H), 1.41(m, 2H), 0.92(t, 3H), 0.84(m, 3H) |
| 2-21 | CH₂CH(Me)Et | H | H | 7.32(d, 1H), 6.59(dd, 1H), 6.52(s, 1H), 4.83(bs, 2H), 4.30(m, 1H), 2.57(m, 1H), 2.33(m, 1H), 1.60-1.10(m, 3H), 0.92(t, 3H), 0.88(d, 3H) |
| 2-22 | CH₂CH₂CHMe₂ | H | F | 7.22(d, 1H), 6.55-6.50(m, 2H), 3.82(br, 2H), 2.66(m, 2H), 1.63(m, 1H), 1.44(m, 2H), 0.93(d, 6H) |
| 2-23 | CH₂CH₂CHMe₂ | H | H | 7.30(d, 1H), 6.59-6.53(m, 2H), 4.27(m, 1H), 2.55(m, 2H), 1.63(m, 1H), 1.43(m, 2H), 0.96(d, 6H) |
| 2-24 | CH₂CH₂CHMe₂ | H | OMe | 7.23(d, 1H), 6.66(d, 1H), 6.52(dd, 1H), 3.80(bs, 2H), 3.42(s, 3H), 2.88(m, 2H), 1.65(m, 1H), 1.50(m, 2H), 0.95(d, 6H) |
| 2-25 | CH₂-c-C₅H₉ | H | F | 7.25(d, 1H), 6.60-6.50(m, 2H), 4.10-3.80(br, 2H), 2.70(dd, 2H), 2.00(m, 1H), 1.80-1.45(m, 6H), 1.18(m, 2H) |
| 2-26 | CH₂-c-C₅H₉ | H | OMe | 7.24(d, 1H), 6.60-6.50(m, 2H), 3.95-3.60(br, 2H), 3.43(s, 3H), 2.95(d, 2H), 1.98(m, 1H), 1.80-1.42(m, 6H), 1.20(m, 2H) |
| 2-27 | CH₂-c-C₅H₉ | H | H | 7.30(d, 1H), 6.59-6.50(m, 2H), 4.33(m, 1H), 2.55(d, 2H), 2.21(m, 1H), 1.80-1.42(m, 6H), 1.19(m, 2H) |
| 2-28 | CH₂-c-C₆H₁₁ | H | F | 7.23(d, 1H), 6.57-6.48(m, 2H), 3.78(bs, 2H), 2.55(t, 2H), 1.8-0.8(m, 11H) |
| 2-29 | CH₂-c-C₆H₁₁ | H | H | 7.30(d, 1H), 6.57(dd, 1H), 6.50(d, 1H), 4.29(m, 1H), 4.20-3.90(br, 2H), 2.42(d, 2H), 1.78-0.89(m, 11H) |

TABLE 3

General formula (III')

$$\text{(III')}$$

| No | Y'm | R[1'] | $^1$H-NMR[CDCl$_3$/TMS, δ (ppm)] or melting point(° C.) |
|---|---|---|---|
| 3-1 | 3-CH$_2$Cl | Me | 8.75(d, 1H), 8.68(d, 1H), 5.14(s, 2H), 4.06(s, 3H) |
| 3-2 | 3-CH$_2$Cl | Et | 8.68(d, 1H), 8.66 (d, 1H), 5.12(s, 2H), 4.53 (q, 2H), 1.48(t, 3H) |
| 3-3 | 3-CH$_2$F | Me | 8.82(d, 1H), 8.71(d, 1H), 5.90(d, 2H), 4.05 (s, 3H) |
| 3-4 | 3-CF$_3$ | Me | 8.85(d, 1H), 8.83(d, 1H), 4.05(s, 3H) |
| 3-5 | 3-CF$_3$ | H | 130-134 |
| 3-6 | 3-CH$_2$Cl | H | 10.50(brs, 1H), 8.92(d, 1H), 8.85(d, 1H), 5.45 (s, 2H) |
| 3-7 | 3-CH$_2$F | H | 10.55(brd, 1H), 8.99(d, 1H), 8.87(d, 1H), 6.19(d, 2H) |

TABLE 4

| No. | $^1$H-NMR[CDCl$_3$/TMS, δ (ppm)] |
|---|---|
| 1-20 | 9.98(s, 1H), 8.69(d, 1H), 8.45(d, 1H), 7.84(d, 1H), 7.61(dd, 1H), 7.51(d, 1H), 3.63(dd, 2H), 3.07(s, 3H), 2.97(d, 2H), 2.29(m, 1H), 1.34(t, 3H), 0.95(d, 6H) |
| 1-38 | 9.67(s, 1H), 8.77(d, 1H), 8.51(d, 1H), 7.84(d, 1H), 7.69(dd, 1H), 7.54(d, 1H), 3.48(s, 3H), 2.94(d, 2H), 2.43(m, 1H), 0.96(d, 6H), 0.36(s, 9H) |
| 1-63 | 9.55(s, 1H), 8.58(d, 1H), 7.82(d, 1H), 7.61(dd, 1H), 7.51(d, 1H), 3.47(s, 3H), 3.06(s, 3H), 2.95(m, 2H), 2.45(s, 3H), 2.30(m, 1H), 0.95(d, 6H) |
| 1-120 | 8.34(s, 1H), 8.11(s, 1H), 7.44(d, 1H), 7.21(s, 1H), 7.11(d, 1H), 4.82(s, 2H), 3.41(s, 3H), 2.82(d, 2H), 2.65(s, 3H), 1.96(m, 1H), 0.73(d, 6H) |
| 1-121 | 8.32(s, 1H), 8.09(s, 1H), 7.49(d, 1H), 7.16(s, 1H), 7.02(s, 1H), 4.82(s, 2H), 4.32(m, 1H), 2.64(s, 3H), 2.43(d, 2H), 1.61(m, 1H), 0.77(d, 6H) |

The agrohorticultural agent, in particular, agrohorticultural insecticides or acaricides, containing a substituted pyrazinecarboxanilide derivative represented by the formula (I) or salt of the present invention as an active ingredient, are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (*Adoxophyes* sp.), Manchurian fruit moth (*Grapholita inopinata*), oriental fruit moth (*Grapholita molesta*), soybean pod border (*Leguminovora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae* crucivora), tobacco budworm (*Heliothis* sp), codling moth (*Laspey resia* pomonella), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), etc.; TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.; DIPTERA including (*Dacus(Zeugodacus) cucurbitae*), oriental fruit fly (*Dacus(Bactrocera) dorsalis*), rice leafminer (*Agnomyza oryzae*), onion maggot (*Delia antiqua*), seedcorn maggot (*Delia platura*), soybean pod gall midge (*Asphondylia* sp.), etc.; TYLENCHIDA including root-lesion nematode (*Pratylenchus* sp.), coffee root-lesion nematode (*Pratylenchus coffeae*), potato cyst nematode (*Globodera rostochiensis*), root-knot nematode (*Meloidogyne* sp,), citrus nematode (*Tylenchulus semipenetrans*), *Aphelenchus* sp. (*Aphelenchus avenae*), chrysanthemum foliar (*Aphelenchoides ritzemabosi*), etc.; and ACARINA including citrus red mite (*Panonychus citri*), fruit tree red spider mite (*Panonychus ulmi*), carmine spider mite (*Tetranychus cinnabarinus*), Kanzawa spider mite (*Tetranychus Kanzawai* Kishida), two-spotted spider mite (*Tetranychus urticae* Koch), pink tea rust mite (*Acaphylla theae*), pink citrus rust mite (*Aculops pelekassi*), purple tea mice (*Calacarus carinatus*), pear rust mite (*Epitrimerus pyri*), etc.

A substituted pyrazinecarboxanilide derivative represented by the general formula (I) or salts thereof of the present invention is used preferably as agrohorticultural insecticides or acaricides. However, the compound exhibits excellent control effect against various insect pests such as insect pests for forest and wood, insect pests for livestock farming, sanitary insect pests, etc. and can be used as pest control agents in various wide fields. Examples of insect pests include: Tabanidae such as *Tabanus rufidens* Bigot; Muscidae such as housefly (*Musca domestica* uicina MACQUART); Gasterophilidae such as horse bot fly (*Gasterophilus intestinalis*); Hypodermatidae such as cattle grub (*Hypoderma bouis* L.); Phoridae such as *Megaselia spiracularis*; Culicidae such as pale house mosquito (*Culex pipiens* pallens), *Anopheles sinensis*, one-striped mosquito (*Aedes albopictus*), and *Aedes japonicus*; Pulicidae such as cat flea (*Ctenocephalides felis*), dog flea (*Ctenocephalides canis*) and human flea (*Pulex irritans*); Ixodidae such as Ixodes ovatus Neumann; Lymantriidae such as *Euproctis similes*; Rhynchophoridae such as rice weevil (*Si-* tophilus zeamais); Vespidae such as *Vespa simillima* xantho-ptera Cameron; Blattellidae such as German cockroach (*Blattela germanica*); Blattidae such as American cockroach (*Periplaneta americana*) and *Periplaneta japonica*; Pthiridae such as public-louse (*Phthirus pubis*); Termitidae such as Japanese termite (*Reticulitermes speratus*) and house termite (*Coptotermes formosanus*); and Ixodidae such as Ixodes persulcatus; and Macronyssidae such as tropical rat mite (*Ornithonyssus bacoti*).

The agrohorticultural agent, in particular, agrohorticultural insecticides or acaricides, containing a substituted pyrazin-ecarboxanilide derivative represented by the formula (I) or salt of the present invention as an active ingredient has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural agent of the present invention can be exhibited by applying the agents to paddy field, field, fruit trees, vegetables, other crops, seeds of flowers and ornament plants, paddy field water, stalks and leaves, or soil at a season at which the insect pests, sanitary pests and/or nematodes are expected to appear, before their appearance or at the time when their appearance is confirmed.

Plants, for which an agrohorticultural agent of the present invention can be used, are not specifically limited and include, for example, plants shown hereinbelow:

Cereals (e.g. rice (*Oryza sativa*), barley (*Hordeum vulgare*), wheat (*Triticum aestivum* L.), rye (*Secale cereale*), oat (*Avena*), maize (*Zea mays* L.), kaoliang, etc.); legume (soybean, adzuki bean, fava bean, bean, peanut, etc.); fruit trees and fruits (apple, citrus fruits, pear, grapes, peach, plum cherry, walnut, almond, banana, strawberry, etc.); vegetables (cabbage, tomato, spinach, broccoli, lettuce, onion, welsh onion, green pepper, etc.); root vegetables (carrot, potato, sweet potato, lotus root, turnip, etc.); crop for processing (cotton, flax (*Linum usitatissimum*), paper mulberry (*Broussonetia kasinoki* SIEB), paperbush (*Edgeworthia papyrifera*), rape (*Brassica napus* L.), beet (*Beta vulgaris*), hop, sugar cane (*Saccharatum officinarum*), sugar beet (*Beta vulgaris* var. *saccharifera*), olive, rubber, coffee, tobacco, tea, etc.); gourd (pumpkin, cucumber, watermelon, melon, etc.); grass (orchard grass, sorghum, timothy, clover, alfalfa, etc.); grass (Korean lawn grass, bent grass, etc.); crop for spicery (lavender (*Lavandula officinalis* CHAIX), rosemary, thyme, parsley, pepper, ginger, etc.); and flowers (chrysanthemum, rose, orchid, etc.).

Recently, gene recombinant crop (herbicide resistant crop, insect pest resistant crop incorporated with insecticidal toxin generating gene, disease resistant crop incorporated with disease resistance inducer producing gene, taste improved crop, preservability improved crop, yield improved crop, etc.), insect sex pheromone (pheromone disrupting chemicals for leaf roller moths, cabbage armyworm, etc.), IPM (integrated pest management) technology using natural enemy insect have been progressed, and pesticide compositions of the present invention can be used in combination with or by systematization with such technologies.

The agrohorticultural agent of the present invention is generally prepared into conveniently usable forms according to an ordinary manner for formulation of agrochemicals.

That is, the substituted pyrazinecarboxanilide derivative represented by the formula (I) or salt of the present invention and, optionally, an adjuvant are blended with a suitable inert carrier in a proper proportion and prepared into a suitable formulation form such as a suspension, emulsifiable concentrate, soluble concentrate, wettable powder, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon [synthetic, high-dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, plastic carriers such as polyethylene, polypropylene, poly (vinylidene chloride) and the like, chemical fertilizers (e.g. ammonium sulfate, ammonium phosphate, ammonium nitrate, urea and ammonium chloride), and compost. These carriers may be used alone or as a mixture thereof.

A material usable as the liquid carrier is selected from materials that have solubility in themselves or which are without such solubility but are capable of dispersing an active ingredient with the aid of an adjuvant. The following are typical examples of the liquid carrier and can be used alone or as a mixture thereof: water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbon (e.g. kerosene and mineral oils), aromatic hydrocarbons (e.g. benzene, toluene, xylene, solvent naphtha and alkyl-naphthalenes), halogenated hydrocarbons (e.g. dichloro-ethane, chloroform, carbon tetrachloride and chloro-benzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination is some cases, or need not be used at all.

To emulsify, disperse, dissolve and/or wet a compound as active ingredient, a surfactant is used. As the surfactant, there can be exemplified polyoxy-ethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxy-methyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products, and adjuvants such as silicone oils may also be used as a defoaming agent.

Adjuvants such as 1,2-benzisothiazoline-3-one, 4-chloro-3,5-xylenol, butyl p-hydroxybenzoate may also be added as a preservative.

Further, if necessary, functional spreading agents, active enhancers such as metabolic decomposition inhibitor like piperonyl butoxide, anti-freezing agents such as propylene glycol, antioxidants such as BHT, ultraviolet absorbers, and the like may also be added.

The content of the compound as active ingredient may be varied as required, and the compound as active ingredient may be used in a proportion properly chosen in the range of 0.01 to 90 parts by weight per 100 parts of the agrohorticultural agents. For example, in dusts, granules, emulsifiable concentrate or wettable powder, the suitable content of the compound as active ingredient is from 0.01 to 50% by weight. In emulsifiable concentrate or flowable wettable powders, it is also from 0.01 to 50% by weight.

The agrohorticultural agent of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agrohorticultural agent of the present invention is varied depending upon various factors such as a purpose, insect pests to be controlled, a growth state of a plant, tendency of insect pests appearance, weather, environmental conditions, a formulation form, an application method, an application site and application time. It may be properly chosen in the range of 0.001 g to 10 kg, preferably 0.01 g to 1 kg, (in terms of the compound as active ingredient) per 10 ares depending upon purposes.

The agrohorticultural agent of the present invention may be used in admixture with other agrohorticultural insecticides, acaricides, nematocides, fungicides, biotic pesticides or the like in order to expand both spectrum of controllable insect pest species and the period of time when effective application are possible or to reduce the dosage. Furthermore, the agrohorticultural insecticide of the present invention may be used in admixture with herbicides, plant growth regulators, fertilizers or the like, depending upon application situations.

As the other agrohorticultural insecticides, acaricides and nematocides, which are used for the above purpose, there can be exemplified agrohorticultural insecticides, acaricides and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphos, Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Cycloprothrin, Ethofenprox, Halfenprox, Silafluofen, Flucythrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatin oxide, Tricyclohexyltin hydroxide, Sodium oleate, Potassium oleate, Methoprene, Hydroprene, Binapacryl, Amitraz, Dicofol, Kersen, Chrorobenzilate, Bromopropylate, Tetradifon, Bensultap, Benzoximate, Tebufenozide, Methoxyfenozide, Pyridalyl, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, Nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (*Bacillus thuringiensis*), Azadirachtin, Rotenone, Hydroxypropyl starch, Levamisole hydrochloride, Metam-sodium, Morantel tartrate, Dazomet, Trichlamide, Pasteuria penetrans, Monacrosporium-phymatophagum, etc.

As the agrohorticultural fungicides used for the same purpose as above, there can be exemplified agrohorticultural fungicides such as Sulfur, Lime sulfur, Copper sulfate basic, Iprobenfos, Edifenfos, Tolclofos-methyl, Thiram, Polycarbamate, Zineb, Maneb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil, Himexazol, Etridiazol, Fluoroimide, Procymidone, Vinclozolin, Iprodione, Triadimefon, Triflumizole, Bitertanol, Ipconazole, Fluconazole, Propiconazole, Diphenoconazole, Myclobutanil, Tetraconazole, Hexaconazole, Tebuconazole, Thiadinil, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl, Fthalide, Tricyclazole, Pyroquilon, Chinomethionat, Oxolinic acid, Dithianon, Kasugamycin, Validamycin, Polyoxin, Blasticidin, Streptomycin, etc.

Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Isouron, Bensulfuron methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacet-methyl, Quizalofop-ethyl, Bentazon, Calcium peroxide, etc.

As to the biotic pesticides, the same effect as above can be expected by using the agrohorticultural agent of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobactor*, nonpathogenic *Erwinia carotovora*,

*Bacillus subtilis*, etc.; and biotic pesticides utilized as herbicides, such as *Xanthomonas campestris*, etc.

In addition, the agrohorticultural agent of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one, (Z)-8-dodecenyl acetate, (Z)-11-tetradecenyl acetate, (Z)-13-icosen-10-one, 14-methyl-1-octadecene, etc.

EXAMPLES

On a substituted pyrazinecarboxanilide derivative of the general formula (I) or an intermediate thereof, that is, a substituted aniline derivative of the general formula (II), explanations are provided below using EXAMPLES, however, the present invention should not be limited to these.

Example 1

Production of 3-isobutyl-4-[1,2,2,2-tetrafluoro-1-(trifluoromethyl)ethyl]aniline (Compound No. 2-9)

3-Isobutylaniline (14.9 g, 0.1 mol) was diluted in a 300 ml mixed solvent of tert-butyl methyl ether-water (1:1), followed by sequentially adding heptafluoroisopropyl iodide (29.6 g, 0.1 mol), tetrabutylammonium hydrogensulfate (3.4 g, 0.01 mol), sodium hydrogen carbonate (8.4 g, 0.1 mol) and sodium dithionite (17 g, 0.1 mol) and stirring overnight at room temperature. The reaction solution was diluted with hexane, followed by washing twice with a 3N HCl solution, and with aqueous sodium bicarbonate and a saturated brine. The solution was dried over magnesium sulfate and concentrated under reduced pressure, and then the residue was purified by using silica gel chromatography (hexane:ethyl acetate=6:1) to obtain 14.9 g of the desired compound.
Yield: 47%
Property: $^1$H-NMR [CDCl$_3$/TMS, δ (ppm)]
7.23 (d, 1H), 6.54 (dt, 1H), 6.51 (d, 1H), 3.90 (bs, 2H), 2.55 (dd, 2H), 1.83 (m, 1H), 0.91 (d, 6H)

Example 2

Production of 3-isobutyl-4-[1-methoxy-2,2,2-trifluoro-1-(trifluoromethyl)ethyl]aniline (Compound No. 2-10)

3-Isobutyl-4-[1,2,2,2-tetrafluoro-1-(trifluoromethyl) ethyl]aniline (1.6 g, 5 mmol) was dissolved in a 28% by weight methanol solution (9.6 g) of sodium methoxide and stirred under heating for 3 hours. After cooling, the reaction solution was poured into ice water, followed by extracting with ethyl acetate and washing with water. The solution was dried over magnesium sulfate and concentrated under reduced pressure, and then the residue was purified by using silica gel chromatography (hexane:ethyl acetate=5:1) to obtain 1.31 g of the desired compound.
Yield: 79%
Property: $^1$H-NMR [CDCl$_3$/TMS, δ (ppm)]
7.25 (d, 1H), 6.71 (d, 1H), 6.54 (dd, 1H), 3.78 (bs, 2H), 3.43 (s, 3H), 2.81 (d, 2H), 2.13 (m, 1H), 0.92 (d, 6H)

Example 3

Production of 3-isobutyl-4-[2,2,2-trifluoro-1-(trifluoromethyl)ethyl]aniline (Compound No. 2-13)

3-Isobutyl-4-[1,2,2,2-tetrafluoro-1-(trifluoromethyl) ethyl]aniline (874 mg, 3 mmol) was dissolved in dimethylsulfoxide (20 ml), followed by portion-wise adding sodium borohydride (340 g, 9 mmol) and stirring at 60° C. for 3 hours. The reaction solution was added with small amount of ice sequentially, followed by dropwise addition of acetic acid. The reaction solution was diluted with ethyl acetate, and washed four times with water. The solution was dried over magnesium sulfate and concentrated under reduced pressure to obtain 830 mg of the desired compound.
Yield: 99%
Property: $^1$H-NMR [CDCl$_3$/TMS, δ (ppm)]
7.30 (d, 1H), 6.57 (dd, 1H), 6.50 (d, 1H), 4.28 (m, 1H), 3.80 (bs, 2H), 2.41 (d, 2H), 1.78 (m, 1H), 0.91 (d, 6H)

Example 4

Production of N-{3-isobutyl-4-[2,2,2-trifluoro-1-(trifluoromethyl)ethyl]pheny}-3-methyl-pyrazine-2-carboxamide (Compound No. 1-17)

3-Methylpyrazine-2-carboxylic acid (138 mg, 1 mmol), 3-isobutyl-4-[2,2,2-trifluoro-1-(trifluoromethyl)ethyl] aniline (299 mg, 1 mmol), 2-chloro-1-methylpyridinium iodide (255 mg, 1 mmol) and triethylamine (303 mg, 3 mmol) were dissolved in tetrahydrofuran (10 ml) and refluxed under heating for 3 hours. The reaction solution was diluted with ethyl acetate, followed by washing with water. The organic layer was dried over magnesium sulfate anhydride, and concentrated under reduced pressure, and then the residue was purified by using silica gel chromatography (hexane:ethyl acetate=2:1) to obtain 290 mg of the desired compound.
Yield: 69%
Property: Melting point 133 to 134° C.

Example 5

Production of N-{3-isobutyl-4-[1-methoxy-2,2,2-trifluoro-1-(trifluoromethyl)ethyl]pheny}-3-methylpyrazine-2-carboxamide (Compound No. 1-18)

The desired compound was obtained by the reaction for 3 hours in the same manner as in Example 4, except that 3-isobutyl-4-[1-methoxy-2,2,2-trifluoro-1-(trifluoromethyl) ethyl]aniline was used instead of 3-isobutyl-4-[2,2,2-trifluoro-1-(trifluoromethyl)-ethyl]aniline.
Yield: 56%
Property: Melting point 118 to 119° C.

Example 6

Production of N-{3-isobutyl-4-[2,2,2-trifluoro-1-(trifluoromethyl)ethyl]pheny}-3-chloropyrazine-2-carboxamide (Compound No. 1-25)

3-Hydroxypyrazine-2-carboxylic acid (154 mg, 1.1 mmol) was dissolved in phosphorus oxychloride (2 ml), followed by adding one drop of pyridine, refluxing under heating for 2 hours. After that, the reaction solution was concentrated under reduced pressure to obtain 3-chloropyrazine-2-carboxylic acid chloride. The compound was added to a tetrahydrofuran solution (10 ml) of 3-isobutyl-4-[2,2,2-trifluoro-1-(trifluoromethyl)ethyl]aniline (299 mg, 1 mmol) and triethylamine (303 mg, 3 mmol) and refluxed under heating for 3 hours. The reaction solution was diluted with ethyl acetate, followed by washing with water. The organic layer was dried over magnesium sulfate anhydride, and concentrated under reduced pressure, and then the residue was purified by using silica gel chromatography (hexane:ethyl acetate=2:1) to obtain 200 mg of the desired compound.

Yield: 46%

Property: Melting point 128 to 129° C.

Example 7

Production of N-{3-isobutyl-4-[2,2,2-trifluoro-1-(trifluoromethyl)ethyl]pheny}-3-methoxy-pyrazine-2-carboxamide (Compound No. 1-28)

The desired compound was obtained by the reaction for 3 hours in the same manner as in Example 4, except that 3-methoxypyrazine-2-carboxylic acid was used instead of 3-methylpyrazine-2-carboxylic acid.

Yield: 71%

Property: Melting point 135.5 to 137° C.

Example 8

Production of N-{3-isobutyl-4-[1-methoxy-2,2,2-trifluoro-1-(trifluoromethyl)ethyl]pheny}-3-methoxypyrazine-2-carboxamide (Compound No. 1-29)

The desired compound was obtained by the reaction for 3 hours in the same manner as in Example 7, except that 3-isobutyl-4-[1-methoxy-2,2,2-trifluoro-1-(trifluoromethyl)ethyl]aniline was used instead of 3-isobutyl-4-[2,2,2-trifluoro-1-(trifluoromethyl)-ethyl]aniline.

Yield: 50%

Property: Melting point 118 to 119° C.

Example 9

Production of methyl 3-chloromethyl-pyrazine-2-carboxylate (Compound No. 3-1)

Methyl 3-methylpyrazine-2-carboxylate (2.44 g, 16 mmol) was dissolved in chloroform (100 ml) and N-chlorosuccinimde (2.14 g, 16 mmol) was added thereto. Then, benzoyl peroxide (110 mg, 70%, 0.32 mmol) was added and refluxed under heating for 30 hours. The reaction solution was cooled, followed by removing undissolved substance by filtration. The filtrate was concentrated under reduced pressure, and the residue was purified by using silica gel chromatography (hexane:ethyl acetate=1:1) to obtain 1.55 g of the desired compound.

Yield: 52%

Property: $^1$H-NMR [CDCl$_3$/TMS, δ (ppm)]
8.75 (d, 1H), 8.68 (d, 1H), 5.14 (s, 2H), 4.06 (s, 3H),

Example 10

Production of methyl 3-fluoromethyl-pyrazine-2-carboxylate (Compound No. 3-3)

Methyl 3-chloromethylpyrazine-2-carboxylate (1.55 g, 8.3 mmol) was dissolved in DMSO (30 ml), followed by adding cesium fluoride (2.52 g, 16.6 mmol) and hexamethyl triamidophosphate (0.3 ml) and heated at 140° C. for 40 minutes while stirring. The reaction solution was cooled, followed by pouring into a diluted HCl solution, extracting with ethyl acetate, and washing with water. The solution was dried over magnesium sulfate, and concentrated under reduced pressure, and then the residue was purified by using silica gel chromatography (hexane:ethyl acetate=2:1) to obtain 0.13 g of the desired compound.

Yield: 9%

Property: $^1$H-NMR [CDCl$_3$/TMS, δ (ppm)]
8.82 (d, 1H), 8.71 (d, 1H), 5.90 (d, 2H), 4.05 (s, 3H)

Example 11

Production of N-{3-isobutyl-4-[1-methoxy-2,2,2-trifluoro-1-(trifluoromethyl)ethyl]pheny}-3-fluoromethylpyrazine-2-carboxamide (Compound No. 1-39)

Methyl 3-fluoromethylpyrazine-2-carboxylate (390 mg, 2.29 mmol) and 3-isobutyl-4-[1-methoxy-2,2,2-trifluoro-1-(trifluoromethyl)ethyl]aniline (750 mg, 2.29 mmol) were stirred, followed by adding a 28% by weight methanol solution of sodium methoxide (4.4 g, 22.9 mmol), heating at 60° C. for 3 hours while stirring, pouring into a diluted HCl solution, extracting with ethyl acetate and washing with water. The reaction solution was dried over magnesium sulfate, and concentrated under reduced pressure, and then the residue was purified by using silica gel chromatography (hexane:ethyl acetate=3:1) to obtain 0.71 g of the desired compound.

Yield: 67%

Property: $n_D$ 1.4829 (27.7° C.)

Example 12

Production of N-isobutyloxycarbonyl-N-{3-isobutyl-4-[1-methoxy-2,2,2-trifluoro-1-(trifluoromethyl)ethyl]pheny}-3-methylpyrazine-2-carboxamide (Compound No. 1-96)

Sodium hydride (32 mg, 60% by weight, 0.8 mmol) was suspended in THF (10 ml) and a THF solution (5 ml) of N-{3-isobutyl-4-[1-methoxy-2,2,2-trifluoro-1-(trifluoromethyl)ethyl]pheny}-3-methylpyrazine-2-carboxamide (300 mg, 0.67 mmol) was dropwise added thereto. The reaction solution was stirred at room temperature for 30 minutes, and was dropwise added with a THF (2 ml) solution of isobutyl chlorocarbonate (110 mg, 0.8 mmol) and stirred for 2 hours. The reaction solution was poured into a diluted HCl solution, followed by extracting with ethyl acetate, and washing with water. The solution was dried over magnesium sulfate, and concentrated under reduced pressure, and then the residue was purified by using silica gel chromatography (hexane: ethyl acetate=3:1) to obtain 0.33 g of the desired compound.
Yield: 90%
Property: $n_D$ 1.4814 (23.2° C.)

Example 13

Production of N-ethoxymethyl-N-{3-isobutyl-4-[1-methoxy-2,2,2-trifluoro-1-(trifluoromethyl)ethyl]pheny}-3-methylpyrazine-2-carboxamide (Compound No. 1-114)

Sodium hydride (32 mg, 60% by weight, 0.8 mmol) was suspended in THF (10 ml) and a THF (5 ml) solution of N-{3-isobutyl-4-[1-methoxy-2,2,2-trifluoro-1-(trifluoromethyl)ethyl]pheny}-3-methylpyrazine-2-carboxamide (300 mg, 0.67 mmol) was added dropwise thereto. The reaction solution was stirred at room temperature for 30 minutes, and was added with a THF (2 ml) solution of chloromethyl ethyl ether (76 mg, 0.8 mmol) and stirred for 5 hours. The reaction solution was poured into a diluted HCl solution, followed by extracting with ethyl acetate, and washing with water. The solution was dried over magnesium sulfate, and concentrated under reduced pressure, and then the residue was purified by using silica gel chromatography (hexane:ethyl acetate=3:1) to obtain 0.24 g of the desired compound.
Yield: 71%
Property: $n_D$ 1.4899 (23.9° C.)

Example 14

Production of N-acetyl-N-{3-isobutyl-4-[1-methoxy-2,2,2-trifluoro-1-(trifluoromethyl)-ethyl]pheny}-3-methylpyrazine-2-carboxamide (compound No. 1-106)

Sodium hydride (32 mg, 60% by weight, 0.8 mmol) was suspended in THF (10 ml) and a THF (5 ml) solution of N-{3-isobutyl-4-[1-methoxy-2,2,2-trifluoro-1-(trifluoromethyl)ethyl]pheny}-3-methylpyrazine-2-carboxamide (300 mg, 0.67 mmol) was added dropwise thereto. The reaction solution was stirred at room temperature for 30 minutes, and was added with a THF (2 ml) solution of acetyl chloride (63 mg, 0.8 mmol) and stirred overnight. The reaction solution was poured into a diluted HCl solution, followed by extracting with ethyl acetate, and washing with water. The solution was dried over magnesium sulfate, and concentrated under reduced pressure, and then the residue was purified by using silica gel chromatography (hexane:ethyl acetate=3:1) to obtain 0.10 g of the desired compound.
Yield: 30%
Property: $n_D$ 1.4955 (23.0° C.)

Example 15

Production of methyl 3-trifluoromethyl-pyrazine-2-carboxylate (Compound No. 3-4)

Methyl 3-chloropyrazine-2-carboxylate (2 g, 11.6 mmol), cuprous iodide (3.3 g, 17.3 mmol), potassium fluoride (1.34 g, 23 mmol) and methyl chlorodifluoroacetate (3.36 g, 18.2 mmol) were dissolved in DMF (20 ml) and stirred at 115° C. for 5 hours under argon atmosphere. The reaction solution was filtered with celite, followed by dilution of the filtrate with ethyl acetate, and washing four times with water. The filtrate was dried over magnesium sulfate, and concentrated under reduced pressure, and then the residue was purified by using silica gel chromatography (hexane:ethyl acetate=3:1) to obtain 700 mg of the desired compound as paste state.
Yield: 29%
Property: $^1$H-NMR [CDCl$_3$/TMS, δ (ppm)] 8.85 (d, 1H), 8.83 (d, 1H), 4.05 (s, 3H)

Example 16

Production of 3-trifluoromethylpyrazine-2-carboxylic acid (Compound No. 3-5)

Methyl 3-trifluoromethylpyrazine-2-carboxylate (700 mg, 3.4 mmol) was dissolved in ethanol-water (1:1, 10 ml), followed by adding potassium hydroxide (300 mg) and refluxing under heating for 1 hour. The reaction solution was concentrated under reduced pressure, followed by dilution of residue with water and washing with ethyl acetate. The water layer was acidified with HCl, followed by extracting with ethyl acetate, washing with a saturated brine. The solution was dried over magnesium sulfate, and concentrated under reduced pressure to obtain 409 mg of the desired compound as crystal.
Yield: 63%
Property: Melting point 130 to 134° C.

Example 17

Production of N-{3-isobutyl-4-[2,2,2-trifluoro-1-(trifluoromethyl)ethyl]pheny}-3-trifluoromethylpyrazine-2-carboxamide (Compound No. 1-42)

3-Trifluoromethyl-2-pyrazine carboxylic acid (192 mg, 1 mmol), 3-isobutyl-4-[2,2,2-trifluoro-1-(trifluoromethyl)ethyl]aniline (199 mg, 1 mmol), 2-chloro-1-methylpyridinium iodide (255 mg, 1 mmol) and triethylamine (303 mg, 3 mmol) were dissolved in THF (10 ml) and refluxed under heating for 2 hours. The reaction solution was diluted with ethyl acetate, followed by washing with water. The organic layer was dried over magnesium sulfate anhydride, and concentrated under reduced pressure, and then the solution was purified by using silica gel chromatography (hexane:ethyl acetate=2:1) to obtain 293 mg of the desired compound as paste state.
Yield: 62%
Property: $n_D$ 1.4825 (27.7° C.)

Typical formulation examples and test example of the present invention are described below but they should not be construed as limiting the scope of the invention.

As used in the examples, the terms "part" and "parts" are by weight.

Formulation Example 1

| | |
|---|---|
| Each compound listed in Table 1 | 10 parts |
| Xylene | 70 parts |
| N-methylprrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| Each compound listed in Table 1 | 3 parts |
| Clay powder | 82 parts |
| Diatomaceous earth powder | 15 parts |

A dust was prepared by mixing uniformly and grinding the above ingredients.

Formulation Example 3

| Each compound listed in Table 1 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| Each compound listed in Table 1 | 20 parts |
| Mixture of kaolin and synthetic kaoline and high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Acaricidal Action on Two-spotted Spider Mite (*Tetranychus urticae*)

Leaf disk having a diameter of 2 cm was prepared by leaves of kidney bean, and the leaf disk was placed on the wetted filter paper. Adult hens of two-spotted spider mite were inoculated on the wetted filter paper, and then 50 ml of a liquid chemical, prepared by diluting a formulation containing each compound listed in Table 1 as an active ingredient to adjust each of the concentrations to 500 ppm and 50 ppm, was sprayed on turntable uniformly. After the spraying, it was allowed to stand in a room thermostatted at 25° C. Two days after the treatment of a liquid chemical, the hatched mites were counted. The mortality was calculated according to the following equation and the acaricidal action was judged according to the criterion shown below. The test was carried out with duplicate groups each of which consists of 10 mites.

$$\text{Corrected mortality}(\%) = \frac{\substack{\text{Number of hatched} \\ \text{mites in untreated} \\ \text{group}} - \substack{\text{Number of hatched} \\ \text{mites in treated} \\ \text{group}}}{\substack{\text{Number of hatched} \\ \text{mites in untreated} \\ \text{group}}} \times 100$$

Criterion:
A—Corrected Mortality 100%
B—Corrected Mortality 99%-90%
C—Corrected Mortality 89%-80%
D—Corrected Mortality 79%-50%

As comparative compounds, compounds Nos. 1-163 and 1-164 disclosed in JP-A-2003-48878 were used.

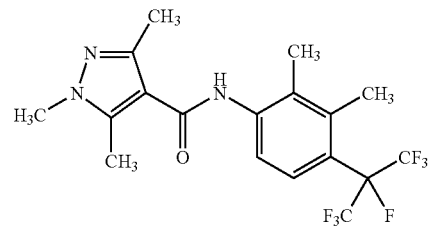

(1-163)

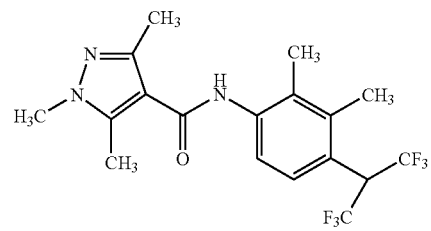

(1-164)

As a result, the following compounds were rated A in all the concentrations of 500 ppm and 50 ppm: compound Nos. 1-2 to 1-4, 1-6 to 1-10, 1-12 to 1-14, 1-17 to 1-30, 1-39, 1-42, 1-43, 1-51, 1-53, 1-54, 1-73, 1-74, 1-76, 1-77, 1-79, 1-81, 1-82, 1-87, 1-90, 1-96, 1-104, 1-106, 1-112, 1-114, 1-117, 1-125, 1-127 to 1-129, 1-134 to 1-138, 1-145, 1-146, 1-153 to 1-160, 1-163, 1-189, 1-199 to 1-210 and 1-213 to 1-222.

On the other hand, both of the comparative compounds did not exhibit the acaricidal action even in the concentration of 500 ppm.

The invention claimed is:

1. A substituted pyrazinecarboxylic acid derivative or salt thereof represented by the general formula (III'):

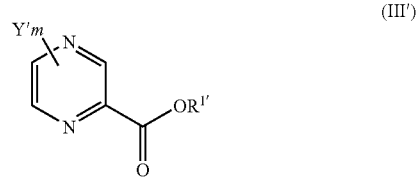

(III')

wherein Y' represents a 3-halo $C_1$-$C_6$ alkyl group; $R^{1'}$ represents a hydrogen atom or a $C_1$-$C_6$ alkyl group; and m represents an integer of 1.

* * * * *